(12) United States Patent
Xie et al.

(10) Patent No.: US 9,964,472 B2
(45) Date of Patent: May 8, 2018

(54) METHODS FOR SAMPLING GINGIVAL METABOLITES

(71) Applicant: The Procter & Gamble Company, Cincinnati, OH (US)

(72) Inventors: Sancai Xie, Liberty Township, OH (US); John Christian Haught, West Chester, OH (US); Cheryl Sue Tansky, Forest Park, OH (US); Thomas Glenn Huggins, Jr., Mason, OH (US); Donald James White, Jr., Fairfield, OH (US); Lijuan Li, Lebanon, OH (US); Malgorzata Klukowska, Mason, OH (US); Angela Marie Fieno, Hamilton, OH (US); Deepa Ashok Khambe, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days. days.

(21) Appl. No.: 15/197,505

(22) Filed: Jun. 29, 2016

(65) Prior Publication Data

US 2018/0003598 A1  Jan. 4, 2018

(51) Int. Cl.
*G01N 1/28* (2006.01)
*A61B 10/02* (2006.01)

(52) U.S. Cl.
CPC .............. *G01N 1/28* (2013.01); *A61B 10/02* (2013.01); *A61B 2010/0216* (2013.01); *A61B 2010/0225* (2013.01)

(58) Field of Classification Search
None
See application file for complete search history.

(56) References Cited

U.S. PATENT DOCUMENTS

| | | | |
|---|---|---|---|
| 5,167,952 A | 12/1992 | McHugh | |
| 5,175,089 A | 12/1992 | Fine et al. | |
| 6,203,990 B1* | 3/2001 | Fahy ........................ | G06F 19/26 204/606 |
| 6,440,087 B1* | 8/2002 | Sangha .............. | A61B 10/0051 600/582 |
| 8,771,962 B2* | 7/2014 | Southern .............. | G01N 33/528 435/7.1 |
| 9,874,573 B2* | 1/2018 | Southern ............ | G01N 33/6893 |
| 2005/0113345 A1 | 5/2005 | Chow et al. | |
| 2007/0160544 A1 | 7/2007 | Sreenivasan | |
| 2009/0047240 A1 | 2/2009 | Johnson et al. | |
| 2009/0305296 A1* | 12/2009 | Bengtsson ....... | G01N 33/56955 435/7.1 |
| 2011/0143365 A1* | 6/2011 | Buchanan ............. | B01L 3/5029 435/7.1 |
| 2012/0014883 A1* | 1/2012 | Scott .................... | A61K 8/0216 424/52 |
| 2012/0019735 A1 | 1/2012 | Zuidema et al. | |
| 2012/0020891 A1* | 1/2012 | Barnes ............... | G01N 33/5038 424/9.7 |
| 2012/0021375 A1 | 1/2012 | Binner et al. | |
| 2014/0243706 A1* | 8/2014 | El-Fahmawi ...... | A61B 10/0045 600/572 |
| 2016/0327557 A1 | 11/2016 | Haught et al. | |
| 2017/0119643 A1 | 5/2017 | Haught et al. | |

FOREIGN PATENT DOCUMENTS

| | | |
|---|---|---|
| CA | 2323630 A1 | 8/1990 |
| EP | 1971865 B1 | 4/2013 |
| GB | 2481267 B | 4/2016 |
| JP | 2006105969 A | 4/2006 |
| JP | 2006109734 A | 4/2006 |
| JP | 2006265212 A | 10/2006 |
| WO | WO1995013094 A1 | 5/1995 |
| WO | WO2007127392 A2 | 11/2007 |
| WO | WO2008042279 A2 | 4/2008 |
| WO | WO2010114537 A1 | 10/2010 |
| WO | WO2011091366 A2 | 7/2011 |
| WO | WO2011158016 A2 | 12/2011 |
| WO | WO2014098868 A1 | 6/2014 |
| WO | WO2015116854 A1 | 8/2015 |

OTHER PUBLICATIONS

Yamada et al. (Oral Microbiol Immunology 2000 col. 15, p. 188-195).*
International Search Report and Written Opinion for PCT/US2017/039226 dated Sep. 12, 2017.
International Search Report and Written Opinion for PCT/US2016/031350 dated Jul. 18, 2016.
International Search and Written Opinion for PCT/US2016/031349 dated Jul. 18, 2016.
All Office Actions, U.S. Appl. No. 15/148,663, filed May 6, 2016.
All Office Actions, U.S. Appl. No. 15/149,044, filed May 6, 2016.
Henkel et al. "Toxins from Bacteria", EXS, (2010) 100:1-30.
Huang, Li-Yun et al., "Use of Toll-Like Receptor Assays to Detect and Identify Microbial Contaminants in Biological Products", Journal of Clinical Microbiology, Nov. 2009, p. 3427-3434.
Liebers, Verena et al. "Occupational Endotoxin-Exposure and Possible health Effects on Human", American Journal of Industrial Medicine 49(6):474-491 (2006).
Madianos, PN et al., "Generation of inflammatory stimuli: how bacteria set up inflammatory responses in the gingiva", J. Clin. Periodontol. 2005; 32(supplement 6): 57-71.
Mullarkey, M. et al. "Inhibition of endotoxin response by E5564, a novel toll like receptor 4 directed endotoxin antagonist", Journal of Pharmacology and Experimental Therapeutics, American Society for Pharmacologoy and Experimental Therapeutics, vol. 304, No. 3, Jan. 1, 2003, pp. 1093-1102.
Offenbacher, S et al., "Gingival transcriptome patterns during induction and resolution of experimental gingivitis in humans", J. Periodontol. Dec. 2009; 80(12): 1963-82.
Raetz et al. "Lipopolysaccharide endotoxin", Annu. Rev. Biochem (2002) 71:635-700.
Rock, FL et al., "A family of human receptors structurally related to *Drosophila* Toll", Proc. National Academy Science, Jan. 20, 1998, 95:588-93.

(Continued)

*Primary Examiner* — Changhwa J Cheu
(74) *Attorney, Agent, or Firm* — Parker D. McCrary; James E. Oehlenschlager

(57) ABSTRACT

One or more methods for sampling gingival metabolites and biomarkers.

10 Claims, 14 Drawing Sheets

(56) References Cited

OTHER PUBLICATIONS

Shapira, L. et al., "Effect of Amine- and Stannous Fluoride on Human Neutrophil Functions in vitro", J. Dent. Res. 73(7): 1381-1386, Jul. 1997.

Sulamain, Ali et al. "Corresponding Author: Bacterial Endotoxin Released by Different Types of Mouthwash", World Applied Sciences Journal, Jan. 1, 2012, pp. 305-309.

Takeuchi, et al., "A novel member of an expanding toll-like receptor family", Gene, Apr. 29, 1999, 231(1-2): pp. 59-65.

Wood, Stewart J. et al., "Anti-Endotoxin Agents. 1. Development of a Fluorescent Probe Displacement Method Optimized for High-Throughput Identification of Lipopolysaccharide-Binding Agents", May 1, 2004, retrieved from Internet on Jun. 23, 2016: URL:http://www.ncbi.nlm.nih.gov/pmc/articles/PMC1540690/pdf/nihms2661.ppdf.

Yokoyama, Yuji et al., "Systemic Immune Response to Streptococcal and Staphylococcal Lipoteichoic Acids in Children with Recurrent Tonsillitis", Acta Otolaryngol (Stockh) 1996; Suppl 523: 108-111.

Zhang, Hongwei et al., "Lipoprotein Release by Bacteria: Potential Factor in Bacterial Pathogenesis", Infection and Immunity, Nov. 1998, vol. 66, No. 11, pp. 5196-5201.

Chuang, TH1 et al., "Cloning and characterization of a sub-family of human toll-like receptors: hTLR7, hTLR8 5 and hTLR9", Eur. Cytokine Netw . . . Sep. 2000, 11(3):372-8).

Darveau, R.P. et al., "Porphyromonas gingivalis Lipopolysaccharide Contains Multiple Lipid A species That Functionally Interact with Both Toll-Like Receptors 2 and 4", Infection and Immunity, vol. 72, No. 9, Sep. 1, 2004, pp. 5041-5051.

Dongari-Bagtzoglou et al., "Production of inflammatory mediators and cytokines by human gingival fibroblasts following bacterial challenge," J. Periodont. Res. 1996; 31:90-98.

Haarmann et al., "Soluble VCAM-1 impairs human brain endothelial barrier integrity via integrin α-4-transduced outside-in signalling," Acta Neuropathol (2015) 129:639-652.

Lamont et al., "Polymicrobial synergy and dysbiosis in inflammatory disease," Trends in Molecular Medicine, Mar. 2015, vol. 21, No. 3, 172-183.

Sandilands et al., "Filaggrin in the frontline: role in skin barrier function and disease," J Cell Sci. May 1, 2009;122(Pt 9):1285-94.

Sartorelli et al., "Carnitine and deoxycarnitine concentration in rat tissues and urine after their administration," Biochim Biophys Act. 1006, (1989), 15-18.

Tannehill et al. "Succinate is an inflammatory signal that induces IL-1β through HIF-1α," Nature 496, 2013, 238-242.

Mabalirajan et al. "Linoleic acid metabolite drives severe asthma by causing airway epithelial injury," Sci Rep. 2013; 3:1349.

\* cited by examiner

FIG. 1. Collection of gingival and buccal samples.

FIG. 2. Clinical measurements: The test regimen group demonstrated significantly (p<0.0001) lower mean bleeding (GBI) and inflammation (MGI) relative to the negative control group at Weeks 1, 3 and 6.

FIG. 3. Changes in the amount of bacterial and host DNA in the supragingival plaques during 6 week of regimen treatment.

FIG. 4. Decreases in bacterial abundance in the supragingival plaques during the six week of regimen treatment.

FIG. 5. Citrulline concentrations decreased in Buccal-brush samples over the period of six-week regimen treatment.

FIG. 6. Protein bound ornithine in Buccal brush samples decreased during treatment.

FIG. 7. Enzymes in the ornithine, citrulline and arginine cycle.

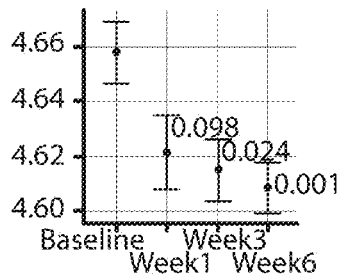
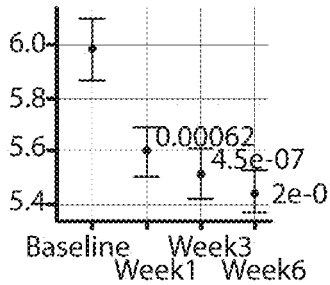
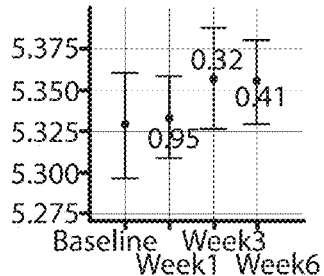
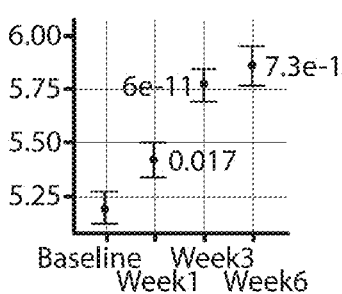
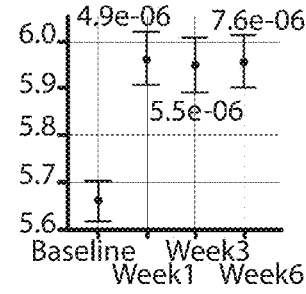
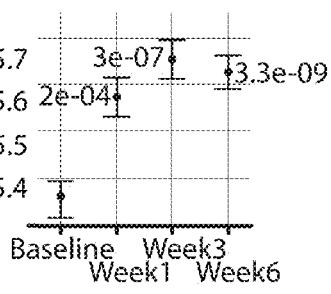
FIG. 8

FIG. 9. Citrulline concentrations increased in Buccal-brush samples in experiment gingivitis.
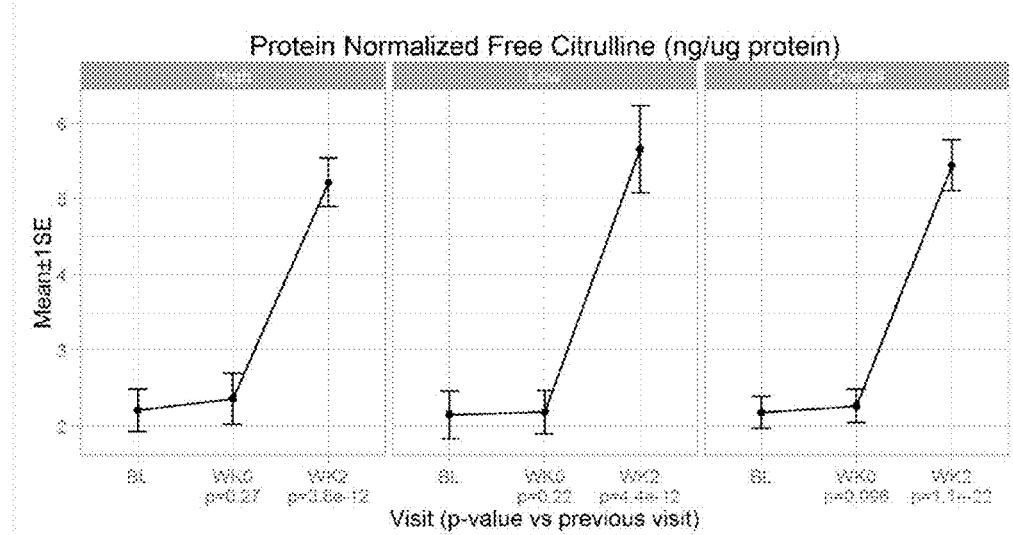

FIG. 10. Protein bound citrulline in Buccal brush samples decreased in experimentally induced gingivitis.
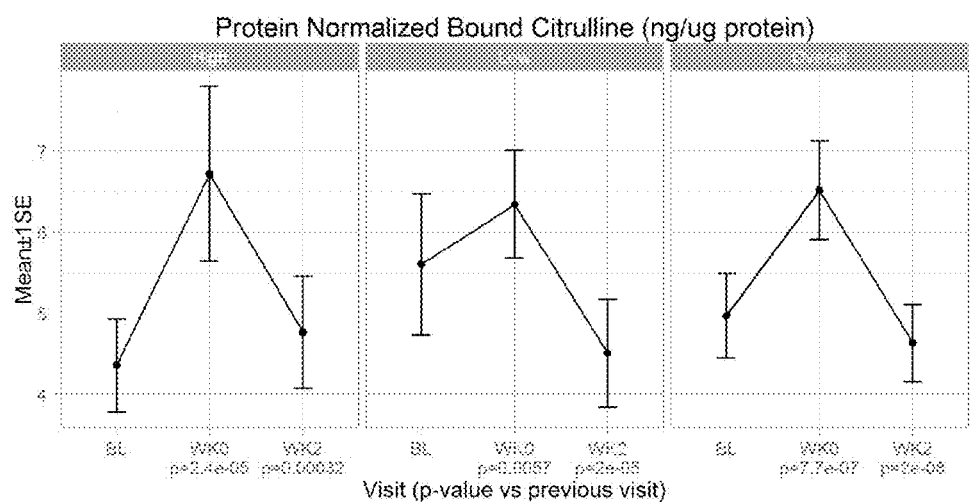

FIG. 11. Concentrations of protein bound ornithine increased in Buccal-brush samples in experimentally induced gingivitis.
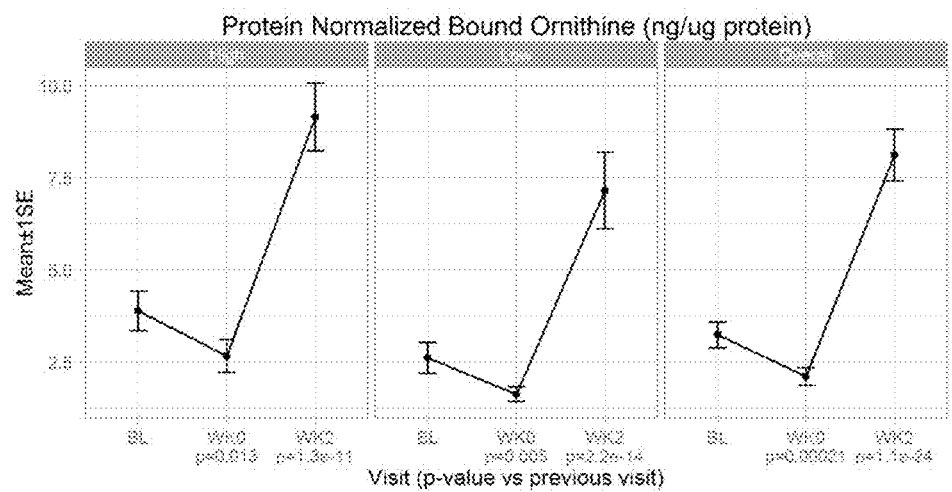

FIG. 12. Concentrations of total citrulline increased in Buccal-brush samples in experimentally induced gingivitis.
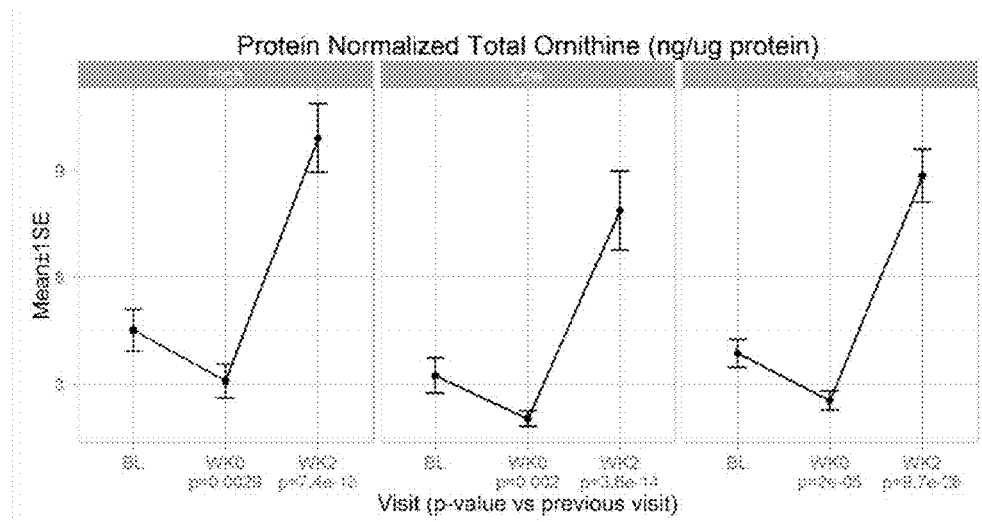

FIG. 13. Concentrations of protein bound arginine decreased in Buccal-brush samples in experimentally induced gingivitis.
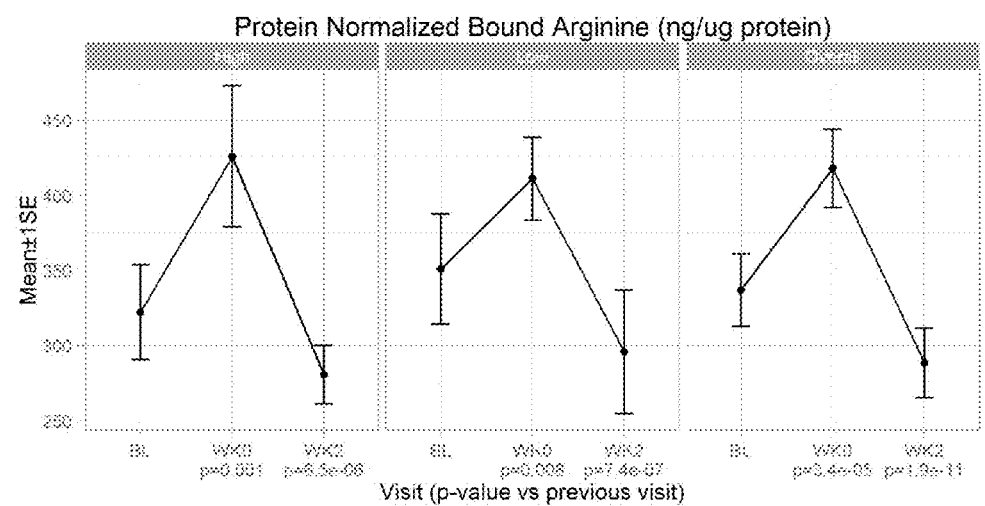

FIG. 14. Concentrations of total arginine decreased in Buccal-brush samples in experimentally induced gingivitis.
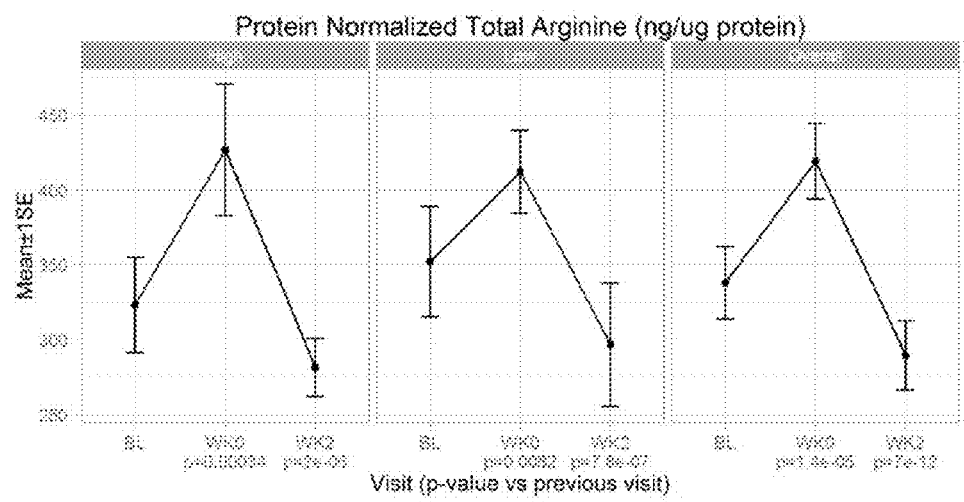

METHODS FOR SAMPLING GINGIVAL METABOLITES

FIELD OF THE INVENTION

The invention is related to methods of collecting gingival samples non-invasively at a specific site, extracting and analyzing metabolites; using metabolites, such as citrulline, ornithine, succinic acid, to monitor the health status of gingivae.

BACKGROUND OF THE INVENTION

Periodontal diseases, such as gingivitis and periodontitis, involve chronic inflammation in the gingival tissue caused by microbial communities and host immune responses. They are one of the most ubiquitous diseases worldwide, and remain the most common cause of tooth loss in the world today, and can affect up to 90% of the population worldwide. Gingivitis is defined per the FDA monograph (12 CFR Part 356, Vol. 68, No. 103 (2003)) as "An inflammatory lesion of the gingiva that is most frequently caused by dental plaque. Gingivitis is characterized by tissue swelling and redness, loss of stippling (a normal state in which the surface of healthy gingiva is comprised of small lobes), glossy surface, and increased tissue temperature. The gingiva also may bleed upon gentle provocation, such as tooth brushing or may bleed spontaneously. Gingivitis is usually not painful." In healthy gingiva, the microbial community is in a homeostatic equilibrium with the host, and host immune systems limit bacterial overgrowth and neutralize toxic products, such as lipopolysaccharides (LPS) and lipoteichoic acids (LTA). The intricate balance between host and bacteria is disrupted as bacteria overgrow in the gingival margins or in the subgingival crevice. Recent data from metagenomics studies showed that bacterial species were increased in supragingival and subgingival plaques, such as *Prevotella pallens, Prevotella intermedia, Porphyromonas gingivalis*, and *Filifactor alocis*. Although the etiology of gingivitis and periodontitis remains elusive, one thing is clear; the composition of the dental plaques is significantly different in healthy sites compared with clinically defined disease sites. This observation, together with advances in characterizing the host and bacterial interactions using the newly developed tools in genomics, proteomics and metabonomics, has led to the notion that gingivitis and periodontitis are the result of disrupted homeostasis between host and polymicrobial communities (Lamont R J and Hajishengallis G. Polymicrobial synergy and dysbiosis in inflammatory disease. G Trends Mol Med. 2015; 21:172-83).

Polymicrobial communities in the dental plaques produce various virulence factors; for example, many bacteria produce digestive enzymes, such as hyaluronidases to breakdown polysaccharides that glue the host cell together, fibrinolytic enzymes that lyse the fibrins of blood clots, and collagenases that degrade collagens in the connective tissues. Gram negative bacteria secrete endotoxins, also called LPS, while Gram positive bacteria produce LTA and peptiglycans. Furthermore, one pathogen bacterium can generate multiple virulence factors; for example *P. gingivalis* has been reported to generate multiple virulence factors that are involved in the inflammatory and destructive events of periodontal tissues. These influence factors include the capsule, outer membrane, its associated LPS, fimbriae, proteinases, and selected enzymes.

LPS is an integral component of all Gram negative bacteria and is found in the outer membrane layer. *P. gingivalis* LPS possesses significant amounts of heterogeneity containing tetra- and penta-acylated structures. Several of them have been purified. LPS 1690 is highly toxic, while LPS 1435/1449 is relatively mild. Chemically, LPS consists of a hydrophilic polysaccharide and a hydrophobic lipid moiety referred to as lipid A. The latter is the actual toxic moiety of the LPS molecule and contains phosphate groups shown to be essential for its proinflammatory activity. Mechanistically, LPS first binds to LPS-binding protein (LBP), then the LBP-LPS complex is transferred to membrane-bound CD14, thereby enabling interactions with Toll-like receptor (TLR) 4 on cell membranes. Binding of LPS to TLR4 on the cell membrane activates both TIRAP-MyD88-dependent NFkB and TRAM-TRIF-dependent IRF3 or IRF7 signaling pathways, and subsequently stimulate production of proinflammatory cytokines and chemokines, such as interferon (IFN) gamma, tumor necrosis factor-$\alpha$ (TNF$\alpha$), interleukin (IL)-1$\beta$, IL-6, IL-8, and IL-12. Also, induced is production of nitric oxide, prostaglandins, leukotrienes, and proteolytic enzymes. Importantly, LPS has been reported to cause periodontitis in mouse and rats.

*P. gingivalis* also secretes exotoxins and enzymes that exert damage on the host following their release. These enzymes include proteases, coagulases, and fibrinolysins. Noticeably, *P. gingivalis* generates peptidylarginine deiminase that can modify free or peptide-bound arginine to citrulline. The citrullinated proteins are especially harmful since they cause auto-immune responses, and are hypothesized to be the culprit of rheumatoid arthritis. In addition, *P. gingivalis* also produces two types of gingipains, lysine specific (Kgp) and arginine specific (Rgps). Gingipains play a major role in stirring up inflammation and tissue destruction in the periodontium.

Peptidoglycan is the cell wall component common to all Gram-negative and Gram-positive bacteria. It is a polymer consisting of sugars and amino acids that form a mesh-like layer outside the plasma membrane. The sugar component consists of alternating residues of $\beta$-(1, 4) linked N-acetylglucosamine and N-acetylmuramic acid. A peptide chain of three to five amino acids is cross-linked to the N-acetylmuramic acid. The peptide chain can also be cross-linked to the peptide chain of another strand of peptidoglycans to weave into a 3D mesh-like layer. The peptidoglycan layer is substantially thicker in Gram-positive bacteria (20 to 80 nanometers) than in Gram-negative bacteria (7 to 8 nanometers). Peptidoglycan accounts for around 90% of the dry weight of Gram-positive bacteria but only about 10% of Gram-negative strains. Thus, presence of high levels of peptidoglycan is the primary determinant of the characterization of bacteria as Gram-positive.

Both peptidoglycans and LTA have been shown to act as inflammatory mediators by activating TLR2 on the cell membrane of host innate immune cells and intracellular signaling receptors, such as nucleotide-binding oligomerization domain or NOD 1 and NOD 2. Binding to TLR2 activates the NF-$\kappa$B signaling pathway, subsequently leading to production and release of proinflammatory cytokines and chemokines, such as IL-1$\alpha$, IL-1$\beta$, IL-6, IL-8, IFN y, and TNF-$\alpha$. Both Gram-negative and positive bacteria and the virulence factors (LPS, peptidoglycans and LTA) induce production of the inducible isoform of nitric oxide synthases. The latter catalyze the production of nitric oxide (NO) from L-arginine. NO is an important cellular signaling molecule, that promotes vascular dilation and many cellular functions. NO is also a free radical with an unpaired electron and is reported to kill bacteria. The inducible isoform of nitric oxide synthases is induced by LPS and other bacterial toxins, and is a part of innate immune responses.

As L-arginine is converted into NO by nitric oxide synthases, a byproduct, citrulline is regenerated. Citrulline is an amino acid that is not encoded in the genetic codes, so that is not incorporated in proteins during translation processes. Its name is derived from citrullus, the Latin word for watermelon. Citrulline is also a key intermediate in the urea cycle, the pathway by which mammals excrete ammonia. Citrulline is synthesized from ornithine and carbamoyl phosphate in the urea cycle, in which urea is produced in a series of reactions. Some of the reactions are carried out in the mitochondrial matrix and others in the cytosol.

The main metabolites of the urea cycle reactions are free amino acids, such as arginine, ornithine, citrulline, and arginisosuccinate. Arginine is the key intermediate in the urea cycle, and in NO production. It is cleaved by the cytosolic enzyme arginase, generating urea and ornithine. Ornithine, formed in the cytosol, is transported to the mitochondrial matrix via the action of ornithine translocase. In the mitochondria, ornithine transcabamoylase (OTC) catalyzes the condensation of ornithine with carbamoyl phosphate, producing citrulline. Concomitant with ornithine transport into the mitochondria is the export of citrulline to the cytosol where the remaining reactions of the cycle take place. Subsequently, citrulline is condensed with aspartate to form arginosuccinate, catalyzed by cytosolic argininosuccinate synthetase. Arginine and fumarate are produced from argininosuccinate by the cytosolic enzyme argininosuccinate lyase (also called argininosuccinase). The fumarate is reconverted to aspartate for use in the argininosuccinate synthetase reaction. In the final step of the urea cycle, arginases break arginine into urea and ornithine. The regenerated cytosolic ornithine is transported to the mitochondrial matrix for another round of urea synthesis. There are two arginase genes in humans, identified as the ARG1 and ARG2 genes. The ARG1 encoded isoform of arginase is a cytosolic enzyme primarily expressed in the liver and functions as the urea cycle enzyme. The ARG2 encoded arginase (arginase-2) is a mitochondrially localized enzyme expressed in non-hepatic tissues, primarily the kidney. The arginase-2 isoform is thought to be involved in nitric oxide and polyamine metabolism, however, the precise role of this enzyme is not clearly defined. More broadly, the biological functions of ornithine, citrulline, arginisosuccinate and arginine are not well understood yet in periodontal health.

Assessing the severity of gingivitis and periodontitis in a person is currently achieved with clinical measures such as gum redness, gum bleeding or pocket depth. While the measures are based on professionally developed scales, the actual values can vary due to examiner differences. There exists a need to quantify how severe gingivitis is and how effective treatments from oral hygiene products are in reducing the inflammatory response. It is desirable to have objective readings from an instrument that is free of human errors. Transcriptomics, proteomics and metabonomics measurements in saliva have been used to diagnose gingivitis, and to monitor progresses in treatment. But there is a disadvantage associated with saliva, in that the composition of saliva will be varied dependent upon the time of collection. As should be apparent, this field has a need for a more sensitive, accurate and consistent test whenever the volunteers appear in a dentist office, or in a clinical setting, or at home.

SUMMARY OF THE INVENTION

A method for non-invasive collection of gingival samples is provided that comprises using a collection device oriented parallel to the gum line of a specific tooth; and a portion of the collection device is detached from the collection device and placed into a container.

A method for extraction from gingival brush samples is provided that comprises using a collection device oriented parallel to the gum line of a specific tooth; a portion of the collection device is detached from the collection device and placed into a container containing extraction buffer; removing the collection device from the container; and extracting a biomarker.

BRIEF DESCRIPTION OF THE DRAWINGS

FIG. 8 shows point graphs illustrating changes in expression of genes that synthesize and ornithine, citrulline and arginine.

FIG. 9 shows line graphs illustrating increased concentrations of citrulline in Buccal-brush samples.

FIG. 10 shows line graphs illustrating decreased protein-bound citrulline in Buccal brush samples.

FIG. 11 shows line graphs illustrating increased concentrations of protein-bound ornithine in Buccal-brush samples.

FIG. 12 shows line graphs illustrating increased concentrations of total citrulline in Buccal-brush samples.

FIG. 13 shows line graphs illustrating decreased concentrations of protein bound arginine in Buccal-brush samples.

FIG. 14 shows line graphs illustrating decreased concentrations of total arginine in Buccal-brush samples.

DETAILED DESCRIPTION OF THE INVENTION

Figure 1:
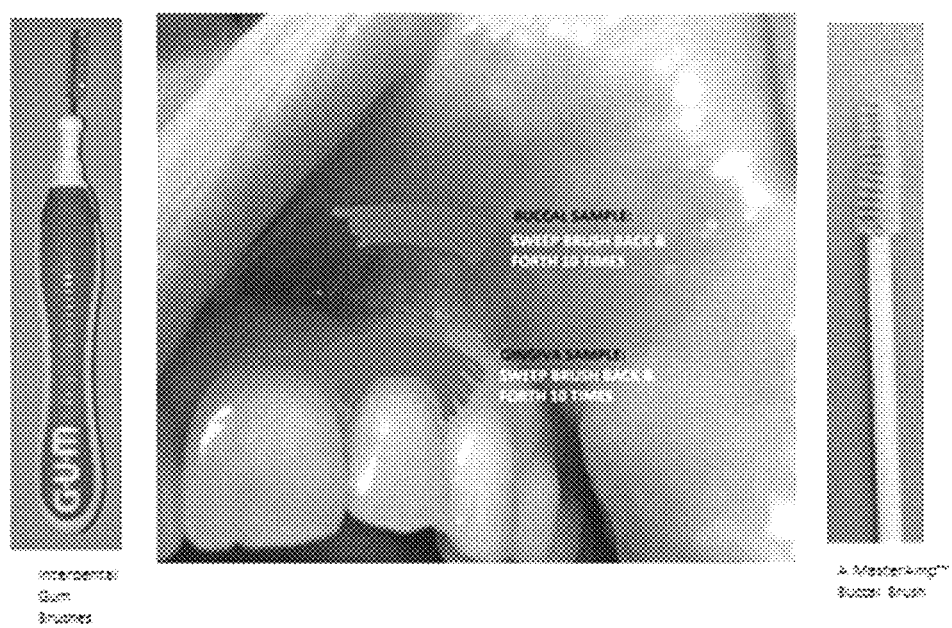
FIG. 1 shows an illustration regarding collection of gingival and buccal samples.

The present invention includes methods of determining the status of epithelial health, particularly gingiva and oral mucosa. A method may comprise determining the levels of a set of biomarkers in gingivae. The set of biomarkers may include one or more metabolites, proteins, or messenger RNA (mRNA). Those metabolites have been shown to change in abundance at particular stages of treatment periods, or in in vitro models treated with different virulence factors, or human dental plaques. Accordingly, the set of metabolite biomarkers may be quantified to determine whether gingivae have inflammation, whether gingivae are under oxidative stresses or energy imbalance, and whether gingivae have cellular damage or injuries.

The present invention demonstrates a role for metabolite biomarkers to serve as indicators of gingivitis at different stages, and indicators for gingivae damage resulting from differing insults, such as oxidative stresses, high bacterial load, proinflammatory insults, energy imbalance or cellular injuries. The methods described herein demonstrate that either elevated or decreased levels of multiple metabolites can be used as a tool for accurately characterizing the quality of gingivae, such as gingivitis.

As used herein, the term "biomarker" means a substance that is measured objectively and evaluated as an indicator of normal biologic processes, pathogenic processes, treatment responses to chemical agents, or mechanical instruments. As used herein, biomarkers include, but are not limited to metabolites, proteins and messenger RNA (mRNA).

As used herein, the term "metabolite" means a substance that is measured objectively and evaluated as an indicator of normal biologic processes, pathogenic processes, treatment responses to chemical agents, or mechanical instruments; wherein said metabolites include, but are not limited to, a compound generated by lipid metabolism, protein metabolism, amino acid metabolism, carbohydrate metabolism, nuclear acid metabolism, or oxidative phosphorylation.

As used herein, the term "protein" means a substance that is measured objectively and evaluated as an indicator of normal biologic processes, pathogenic processes, treatment responses to chemical agents, or mechanical instruments; wherein the protein is a polymer consisting of more than three amino acids, including, but not limiting to, cytokines, chemokines, growth factors, cellular and extracellular proteins.

As used herein, the term "mRNA" means a substance that is a polymer of four ribonucleotides (adenine, uracil, guanine, cytosine), messenger RNA (mRNA) molecules convey genetic information from DNA to the ribosome, where they specify the amino acid sequence of the protein products of gene expression.

As used herein, the term "sample" means biological material isolated from an individual; wherein gingival samples are isolated from gingivae, and buccal samples are isolated from oral mucosa.

As used herein, the term "gum sensitivity" is a sensorial feeling, caused by activating transient receptor potential channel (TRP) V1 and/or TRPA1 on sensory neurons. Gum sensitivity is a common complaint due to inflammation, and can affect the area covering one or more teeth. Gum sensitivity is often noted when one eats or drinks something hot, cold, sweet, or sour; and can be experienced as a dull or sharp pain. The pain can begin suddenly and be felt deeply in the nerve endings of the tooth. Certain polyunsaturated fatty acids (PUFA), such as linoleic acid, arachidonic acid, hydroxyoctadecadienoic acid (HODE), and hydroxyeicosatetraenoic acid (HETE), are known to activate or sensitize TRPV1 and TRPA1. Certain oxidized lipids also activate TRPV1 and TRPA1 on sensory neurons, such as hydroxyoctadecadienoic acid (HODE) and hydroxyeicosatetraenoic acid (HETE), Prostaglandins, prostacyclins, and thromboxanes (Ruparel et al. Released lipids regulate Transient Receptor Potential Channel (TRP)-dependent oral cancer pain. Mol Pain. 2015; 11: 30).

As used herein, the term "oxidative stress" is a threshold criteria based on volunteers exhibiting an imbalance between the production of free radicals and the ability of the body to counteract or detoxify the reactive intermediates or to repair the resulting damage.

As used herein, the term "energy imbalance" or the term "mitochondrial dysfunction" means an imbalance of energy homeostasis. Mitochondria are found in every nucleated cell of the human body, and convert the energy of carbohydrate and fat into the ATP that powers most cellular functions. Both the citric acid cycle and β-oxidation of fatty acids are carried out in mitochondria. In gingivitis where gingivae are inflamed or damaged, AMP levels are high, meaning ATP production is impaired. Similarly, carnitine is a cofactor that helps carry fatty acid into mitochondria. Deoxycarnitine is an immediate precursor of carnitine.

As used herein, the term "barrier function" means the defense function of epithelium against the environment, such as heat, dust, and microbes.

As used herein, the term "immunoassay" means any assay based on antibody-binding-to-specific targets, including, but not limiting to, ELISA (enzyme-linked immunosorbent assay) and immunoblotting. The targets can include, but are not limited to, proteins, peptides, fatty acids, carbohydrates, metabolites, and nucleic acids.

Certain embodiments of the present invention provide a method for collection of gingival samples. Gingival tissues are taken around the tooth, or around the connecting areas between the gingiva and the tooth. In one or more embodiments, a collection device, such as an interdental gum brush or buccal brush is used to collect gingival samples by swabbing back and forth multiple times with the brush-head oriented parallel to the gum line. A portion of the collection device that contacted the connecting areas between the gingiva and tooth may be detached and placed into a container; for example a brush head may be clipped off with a pair of sterile scissors and placed into a container, which may contain a buffer solution or an RNAlater solution.

Included in the present invention are the findings that some protein biomarkers are decreased over time in gingivitis treatment, suggesting those protein biomarkers are associated with gingivitis, inflammation, sensitivity, energy imbalance, mitochondrial dysfunction, and oxidative stresses. Examples of protein biomarkers include ICAM-1, IL-1α, IL-β, TNF-β, IL-12p12, IL-13, IL-4, IL-5, CRP, eotaxin, GM-CSF, IFN-y, IL-10, IL-15, IL-16, IL-6, IL-7, IL-8, MCP-1/CCL2, MDC, SAA, tie-2, VCAM-1, VEGF, VEGF-2, VEGF-D, VEGF-C, and TARC/CCL17.

This application also identifies metabolites in the gingivae that are associated with gingivitis. Changes in metabolites 13-HODE, 9-HODE, 1-arachidonoylglycerophosphoethanolamine, 1-oleoylglycerophosphoethanolamine, citrulline and ornithine occur as the health status of gingival tissue improves or deteriorates. Subgingival bacteria in gingivitis sites stimulated production of ornithine, citrulline, arginine, succinate, fumarate and malate in human peripheral blood mononuclear cells (PBMC). Similarly, endotoxins and LTA also stimulated their production in PBMC to some degree. Those bacteria virulence factors are known to cause inflammation, oxidative stresses, and cellular damages.

Various lipid metabolites have been implicated in different inflammatory diseases. Although much is known about prostaglandins, much less attention has been given to other lipid metabolites. 13-HODE and 9-HODE are stable oxidation products of linoleic acid, the generation of which is increased where oxidative stress, inflammation, and epithelium damage are increased. 13-HODE is produced in large quantities during mitochondrial degradation steps in RBC maturation, whereas 13-hydroxy-linoleic acid, a related molecule, has been linked to airway hyperresponsiveness. 13-HODE is considered as a potential link between mitochondrial dysfunction, epithelial injury, and inflammatory disease (Ulaganathan Mabalirajan et al. Linoleic acid metabolite drives severe asthma by causing airway epithelial injury. *Scientific Reports* 3, Article number: 1349 (2013) doi:10.1038/srep01349).

This invention also describes in the gingivae an increase of adenosine 5'-monophosphate (AMP), 2-methylbutyryl-carnitine (C5), deoxycarnitine, and propionylcarnitine, which is indicative of mitochondrial disfunciton. Bacterial endotoxins, such as LPS, induce the 'Warburg effect' of aerobic glycolysis (Tannahill et al., Succinate is an inflammatory signal that induces IL-1b through HIF-1a, *Nature* 496, 238-242, 2013).

Figure 2:
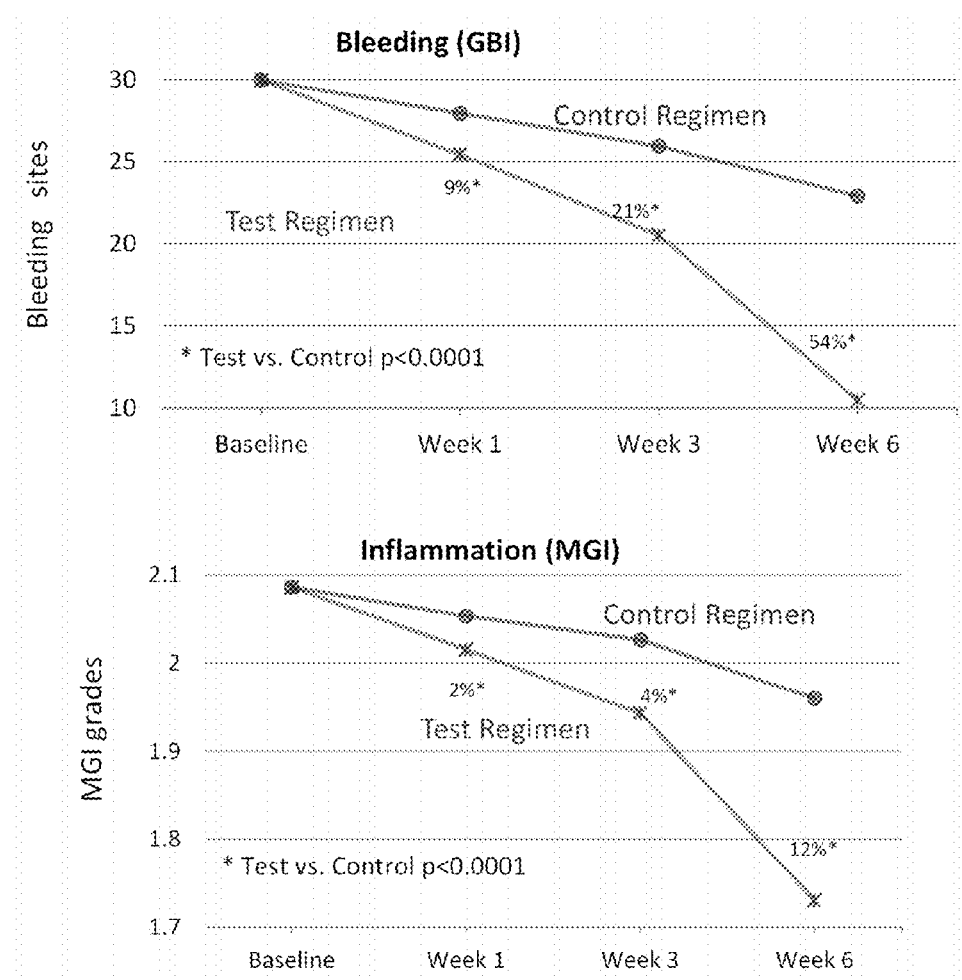
FIG. 2 shows a line graph depicting clinical measurements.

In certain embodiments, this invention communicates the decrease of 2-methylbutyrylcarnitine (C5), deoxycarnitine, and propionylcarnitine in gingivae during treatment over a time period, such as a six week period. As shown in FIG. 2, gingivitis symptoms of bleeding and inflammation are diminished during the treatment period. The decrease of 2-methylbutyrylcarnitine (C5), deoxycarnitine, and propionylcarnitine is indicative of improvement of energy production or mitochondrial dysfunction. Carnitine, which is derived from deoxycarnitine transports long-chain acyl groups from fatty acids into the mitochondrial matrix, so they can be broken down through β-oxidation to acetyl CoA to produce ATP via the citric acid cycle. Supply of deoxycarnitine caused an increase of carnitine. The latter treatment also produced a transient but significant diminution of L-carnitine in heart, skeletal muscle and kidney (Sartorelli et al., Carnitine and deoxycarnitine concentration in rat tissues and urine after their administration. Biochim Biophys Acta. 1989 Nov. 6; 1006:15-8.). Increase of deoxycarnitine in gingivitis likely reduces L-carnitine levels, thus disturbing the β-oxidation and mitochondrial functions. Increase of deoxycarnitine in gingivitis likely changes L-carnitine levels, thus disturbing the β-oxidation and mitochondrial functions.

In gingivitis there is an increase in propionylcarnitine. Propionylcartitine is a byproduct of a branched-chain amino acid (BCAA). BCCA is an amino acid having aliphatic side-chains with a branch (a central carbon atom bound to three or more carbon atoms). Among the proteinogenic amino acids, there are three BCAAs: leucine, isoleucine and valine. Degradation of BCCA involves the branched-chain alpha-keto acid dehydrogenase complex. A deficiency of this complex leads to a buildup of the branched-chain amino acids (leucine, isoleucine, and valine) and their toxic by-products in the blood and urine, giving the condition the name maple syrup urine disease. Accumulation of propionylcartnitine is indicative of disturbed metabolism of BCAA.

One of the most observed symptoms of gingivitis is bleeding, which is partially the result of a damaged vasculature and epithelial barrier. ICAM-1 also known as CD54 (Cluster of Differentiation 54) is a cell surface glycoprotein that is typically expressed on endothelial cells and cells of the immune system. This protein is an intercellular adhesion molecule continuously present in low concentrations in the membranes of leukocytes and endothelial cells. Upon cytokine stimulation, the concentrations greatly increase in the vascular endothelium, macrophages, and lymphocytes. ICAM-1 is a ligand for LFA-1 (integrin), a receptor found on leukocytes. When activated, leukocytes bind to endothelial cells via ICAM-1/LFA-1 and then transmigrate into tissues. Because of these associations with immune responses, it has been hypothesized that ICAM-1 could function in signal transduction. ICAM-1 ligation produces proinflammatory effects such as inflammatory leukocyte recruitment. Importantly, ICAM-1 has antagonistic effects on the tight junctions, which forms the blood-testis barrier. ICAM-1 has been implicated in subarachnoid hemorrhage. Levels of ICAM-1 are shown to be significantly elevated in patients with subarachnoid hemorrhage over control volunteers in many studies.

The VCAM-1 gene contains six or seven immunoglobulin domains, and is expressed on both large and small blood vessels upon being stimulated by proinflammatory cytokines. It is alternatively spliced into two known RNA transcripts that encode different isoforms in humans. VCAM-1 is a cell surface sialoglycoprotein that mediates the adhesion of lymphocytes, monocytes and basophils to vascular endothelium. Human brain microvascular endothelial cells that form the blood-brain barrier release soluble vascular cell adhesion molecule-1 (sVCAM-1) under inflammatory conditions. Similarly, human brain endothelium also expresses integrin α-4/β-1, which binds to sVCAM-1. Binding of integrin α-4/β-1 to sVCAM-1 directly impairs blood-brain barrier function by triggering intracellular signaling events. Application of recombinant sVACM-1 to cultured primary brain endothelial cells increased permeability to the soluble tracer dextran as a result of damaged tight-junctions between endothelial cells (Haarmann et al. Soluble VCAM-1 impairs human brain endothelial barrier integrity via integrin α-4-transduced outside-in signaling, Acta Neuropathologica. May 2015, Volume 129, pp 639-652). ICAM-1 and VCAM-1 are high in gingivae having gingivitis.

Changes in bound arginine, ornithine and citrulline are indicative of damages in barrier function during gingivitis in gingiva tissues. Profilaggrin is the major component of the keratohyalin granules within epidermal granular cells in epidermis and gingivae. During epithelial terminal differentiation, the profilaggrin polyprotein is dephosphorylated and rapidly clipped by serine proteases into monomeric filaggrin. Filaggrin binds to the keratin cytoskeleton and thereby contributes to the squame biogenesis. Within the squames, filaggrin is citrullinated by peptidylarginine deiminase where an arginine residue is converted into a citrulline residue. Arginine is positively charged, while citrulline is neutral in charge. Positively charged arginine forms salt bonds with neighboring negatively charge amino acid residues to stabilize filaggrin proteins. Modification of positively charged arginine into a neutral amino acid residue, such as citrulline or ornithine, will diminish the salt bonds within a protein, thus leading to destabilizing and unfolding proteins, and finally degrading into hygroscopic amino acids. Those amino acids constitute one element of natural moisturising factors. As a result, citrullination is a required process in epidermal differentiation and barrier formation. Strong barrier functions protect the body from the entry of foreign environmental substances. (Sandilands et al., Filaggrin in the frontline: role in skin barrier function and disease. J Cell Sci. 2009 May 1; 122(Pt 9):1285-94. doi: 10.1242/jcs.033969).

In certain embodiments the present invention involves one or more methods for determining the expression of genes for the citric acid cycle, β-oxidation, and oxidative phosphorylation The citric acid cycle, also known as the tricarboxylic acid cycle, is a series of chemical reactions inside a cell to generate energy through the oxidation of acetyl-CoA derived from carbohydrate, fat and proteins into carbon dioxide and chemical energy in the form of ATP. In addition, the cycle provides the reducing agent NADH that is used in numerous other biochemical reactions. β-oxidation is the catabolic process by which fatty acid molecules are broken down in the mitochondria to generate acetyl-CoA, which enters the citric acid cycle, and NADH and $FADH_2$, which are co-enzymes used in the electron transport chain. Oxidative phosphorylation (or OXPHOS in short) is the metabolic pathway in which the mitochondria in cells use their structure, enzymes, and energy released by the oxidation of carbohydrate, fatty acid and amino acid to form ATP.

In certain aspects, this invention describes an increase in degradation of macromolecules in gingivitis, such as proteins. There are more dipeptides in gingivitis at the baseline stage, such as threonylphenylalanine, threonylleucine, lysylleucine, lysylphenylalanine, leucylleucine, arginylphenylalanine, and arginylleucine. This degradation of proteins is indicative of increased production of proteases in inflammation.

EXAMPLES

The term "free" means a substance that is measured in supernatants directly as described in the EXAMPLES.

The term "total" means a substance that is measured in both supernatants and pellets as described in the EXAMPLES.

The term "bound" means a substance that is incorporated into proteins as described in the EXAMPLES. For example, bound citrulline means a citrulline molecule is incorporated into a protein. The bound citrulline is numerically equal to the total citrulline minus the free citrulline.

Example 1—a Method to Collect Host Gingival Tissue from Above Individual Teeth to Assess Changes in Gingivitis-Related Molecular Markers Assessing the degree of gingivitis in a person is typically achieved with clinical measures such as gum redness, gum bleeding or pocket depth. While the measures are based on professionally developed scales, the actual values can vary due to examiner differences. It is desirable to have objective readings free from human errors. This sample collection method enabled the taking of samples for objective measurements non-invasively and site-specifically.

Figure 6:
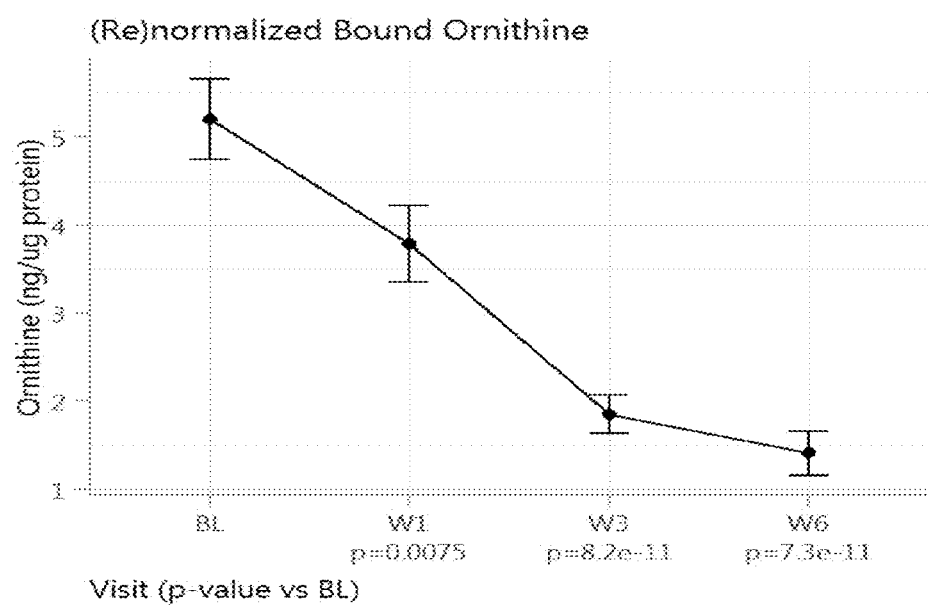
FIG. 6 is a line graph showing a decrease in protein bound ornithine in Buccal brush samples.

Non-invasive gingival sample collection: Brush samples were taken from the upper, front gums and buccal surface of 4 volunteers, all female, ages 43-48. Interdental Gum Brushes (Sunstar America Inc, Chicago, Ill.), or A Master-Amp™ Buccal Brush (Catalog #MB100SP; Epicentre Technologies Corp., Madison, Wis.) brushes were used to sample 6 marginal gingiva, as shown in FIG. 1, and 6 buccal areas, one brush per sample site. At each sample site a brush was swabbed back-forth 10 times with the brush-head horizontally oriented parallel to the gum line. Each brush head was clipped off with sterile scissors and placed into a 15 ml conical tube with 800 µl DPBS (Dulbecco's phosphate-buffered saline; Lifetechnologies, Grand Island, N.Y.) containing protease inhibitors, including AEBSF (4-(2-Aminoethyl) benzenesulfonyl fluoride hydrochloride) 2 mM, aprotinin 0.3 µM, Bestatin 130 µM, EDTA (Ethylenediaminetetraacetic acid) 1 mM, E-64 1 µM, and leupeptin 1 µM.

Metabolites and protein extraction from gingival samples: All gingival swabs from a given volunteer were pooled into the same collection tube. Similarly all buccal swabs from a given volunteer were pooled into a separate, single collection tube. All collection tubes were vigorously shaken on a multi-tube vortexer for 15 min at 4° C. to extract materials, including metabolites and proteins, from the harvested gingival and buccal samples. Using sterile tweezers the brush heads were dabbed to the side of the tube to collect as much lysate as possible and subsequently discarded. The extracted materials were then centrifuged at 5000 RPM (revolutions per minute) in a Refrigerated at 4° C. table top centrifuge Sigma 4k15 (SIGMA Laborzentrifugen GmbH P.O. Box 1713-37507 Osterode/Germany) to separate the soluble and insoluble fractions. The separated samples were stored at −80° C. in a freezer.

Upon analysis of the samples for total protein the samples appeared to have sufficient protein for further analysis, such as proteomics or metabonomics. Interdental gum brushes appeared to collect enough gingival tissue for further quantifiable molecular analysis.

Example 2—Gingivitis-Enriched Bacteria were Reduced in Abundance in Six Week of Gingivitis Treatment A randomized, parallel group clinical study was conducted with 69 volunteers (35 in the negative control group and 34 in the test regimen group). Volunteers were 39 years old on average, ranging from 20 to 69, and 46% of the volunteers were female. Treatment groups were well balanced, since there were no statistically significant ($p \geq 0.395$) differences for demographic characteristics (age, ethnicity, gender) or starting measurements for Gingival Bleeding Index (GBI); mean=29.957 with at least 20 bleeding sites, and Modified Gingival Index (MGI); mean=2.086. All 69 volunteers attended each visit and completed the research. The following treatment groups were compared over a 6-week period: Test regimen: Crest® Pro-Health Clinical Plaque Control (0.454% stannous fluoride) dentifrice, Oral-B® Professional Care 1000 with Precision Clean brush head and Crest® Pro-Health Refreshing Clean Mint (0.07% CPC) mouth rinse. Control regimen (negative control): Crest® Cavity Protection (0.243% sodium fluoride) dentifrice and Oral-B® Indicator Soft Manual toothbrush.

The test regimen group demonstrated significantly ($p<0.0001$) lower mean bleeding (GBI) and inflammation (MGI) relative to the negative control group at Weeks 1, 3 and 6 as shown in FIG. 2.

Dental plaques were also collected from the same volunteers in the test regimen in this clinical study. A supragingival sample was taken from each volunteer with a sterile curette at the tooth/gum interface, using care to avoid contact with the oral soft tissue. Plaques were sampled from all available natural teeth (upper arch only) until no plaque was visible. Following sampling, plaques were released from the curettes by shaking with into a pre-labeled (volunteer ID, sample initials, visit, and date) Eppendorf tube 1.5 ml with 1 ml of PBS/Glycerol buffer (20% glyceroal) and about 30 sterile 1 mm glass beads stored on ice until all samples were collected. The samples were then transferred to a −70° C. freezer for storage until further processing. Genomic DNA was isolated from supragingival plaque samples using QIAamp® genomic DNA kits (Qiagen, Valencia, Calif.) following manufacturer's instruction. Metasequencing was carried out in BGI Americas Corporation (Cambridge, Mass.). All data was analyzed at Global Biotech of Procter & Gamble Company in Mason, Ohio.

Figure 3:
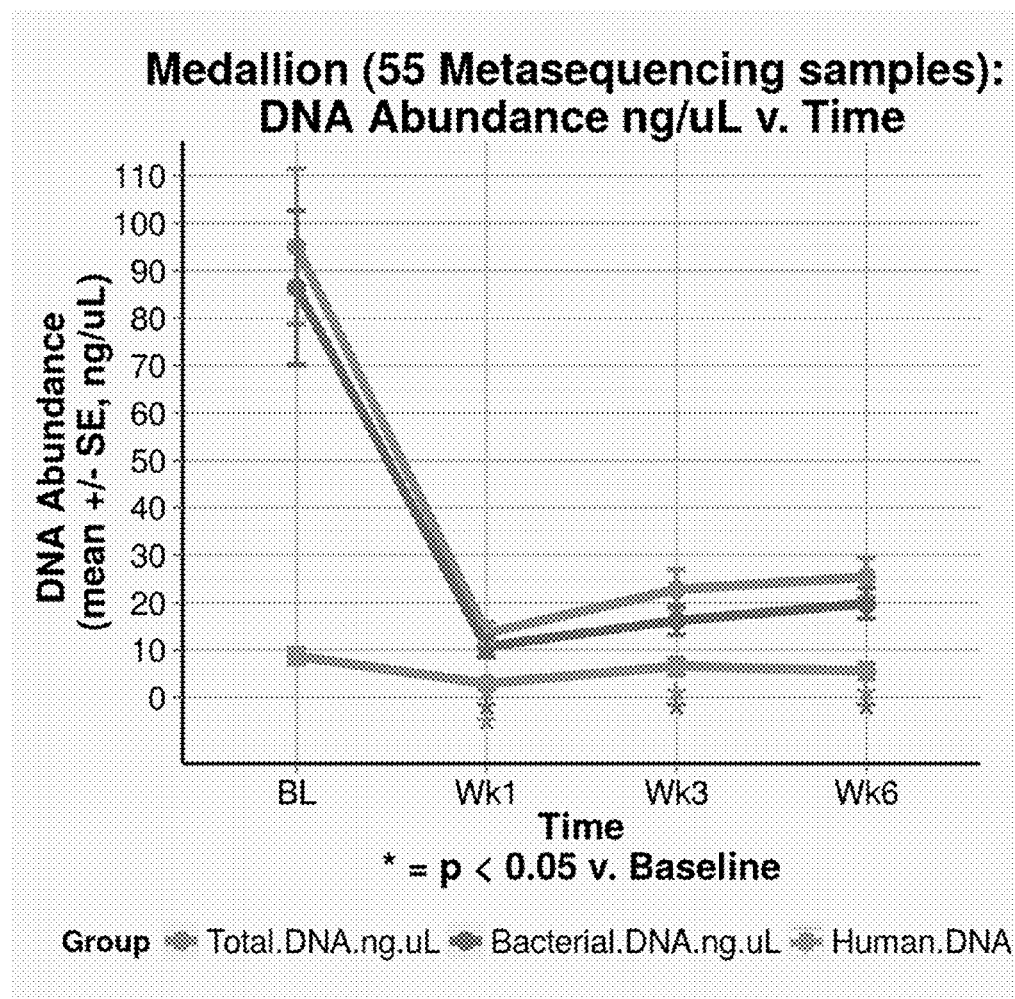
FIG. 3 Changes in the amount of bacterial and host DNA in the supragingival plaques during 6 week of regimen treatment.
Figure 4:
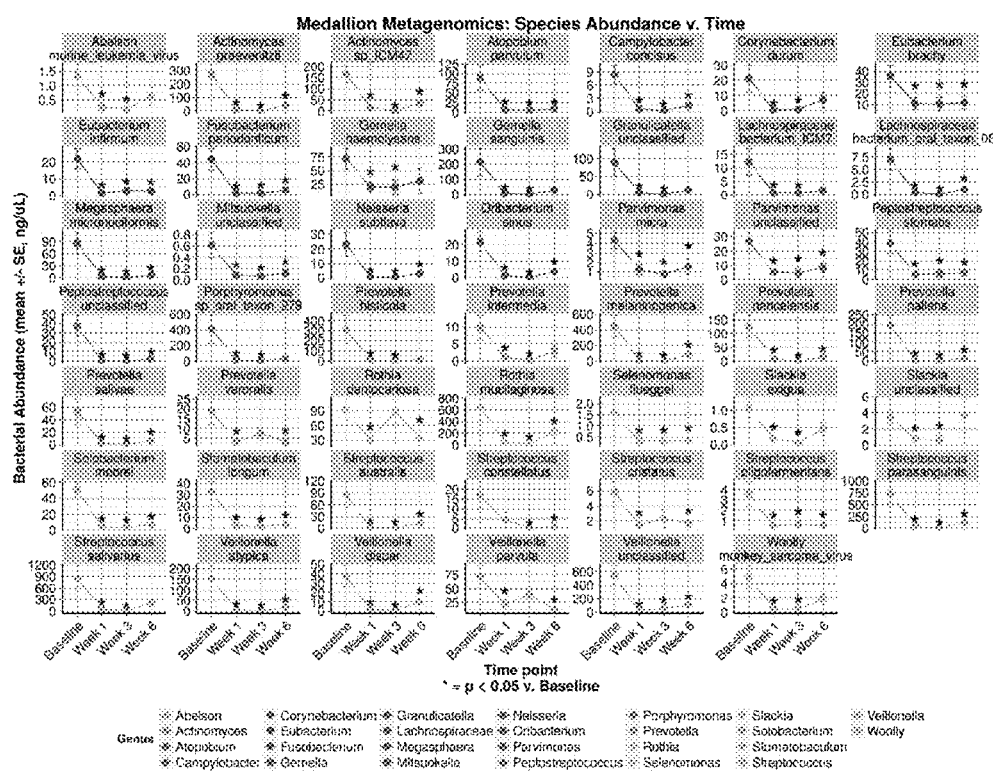
FIG. 4 comprises line graphs showing decreases in bacterial abundance in supragingival plaques.

The Amount of bacterial and host DNA was changed in the supragingival plaques in the 6 week treatments as shown in FIG. 3. Certain bacteria, such as *Porphyromonas* sp *oral taxon* 279 and *Prevotella pallens*, were decreased in weeks 1 and 3 (FIG. 4). The amount of each bacterial species was plotted over the four time periods of the treatment. The amount of certain bacteria, such as *Peptostreptococcus stomatis* and *Prevotella intermedia* was reduced from baseline to week 3. The amount of *Prevotella intermedia* was not statistically different at week 6 from the baseline in relative percentage abundance, but the absolute abundance of *Prevotella intermedia* was far lower at week 6 than at baseline since the total amount of bacterial DNA decreased dramatically at week 6 (FIGS. 3 and 4).

Example 3—Production of Cytokines, Chemokines and Other Bioactive Proteins Decreased as Gingivitis Symptoms were Alleviated During 6 Weeks of Treatment Gingival-brush samples were collected using the procedures described in EXAMPLE 1, from the same volunteers as in EXAMPLE 2. Before sampling, volunteers rinsed their mouths for 30 seconds with water. A dental hygienist then sampled the area just above the gumline using a buccal swab brush (Epicentre Biotechnologies, Madison, Wis., cat. #MB100SP). The swab was immediately placed into 1 ml extraction buffer [PBS, 0.25M NaCl, 1× Halt™ Protease Inhibitor Single-Use Cocktail (Lifetechnologies, Grand Island, N.Y.)] in a 1.5 ml Eppendorf tube vortexed for 30 seconds, and immediately frozen on dry ice and stored in a −80 C freezer until analysis. The samples were taken out of the freezer, thawed and extracted by placing the samples on a tube shaker for 30 minutes at 4° C. The tubes were centrifuged at 15000 RPM for 10 min in Eppendorf Centrifuge 5417R (Eppendorf, Ontario, Canada) to pellet any debris. The extract (800 µl) was analyzed for protein concentrations using the Bio-Rad protein assay (BioRad, Hercules, Calif.).

Forty proteins were measured in the gingival samples using V-PLEX Human Biomarker 40-Plex Kit (Meso Scale Diagnostics Rockville, Md.). The assay was performed following the manufacturer's instruction.

V-PLEX Human Biomarker 40-Plex Kit was divided into four panels, or four 96-well plates. Among the proteins measured in the gingival samples, most proteins had significant changes in their abundance during the 6-week treatment (TABLE 1). Those include FN-γ, IL-1β, IL-2, IL-4, IL-6, IL-8, IL-10, IL-12p70, IL-13, TNF-α, GM-CSF, IL-5, IL-16, IL-7, IL-12/IL-23p40, IL-1α, VEGF-A, IL-17A, IL-15, TNF-β, IL-8 (HA), MCP-1, MCP-4, Eotaxin, IP-10, MDC, Eotaxin-3, TARC, MIP-1α, MIP-1β, VEGF-C, VEGF-D, Tie-2, Flt-1/VEGFR1, P1GF, FGF (basic), SAA, CRP, VCAM-1, and ICAM-1. ICAM-1 and VCAM-1 are high in gingivae having gingivitis, as shown in TABLE 1.

TABLE 1

Changes in abundance of proteins in the gingival-brush samples.

| | Mean | | | | α = 0.05 | | | |
|---|---|---|---|---|---|---|---|---|
| | Baseline | Week 1 | Week 3 | Week 6 | Baseline | Week 1 | Week 3 | Week 6 |
| ICAM-1 | 16.035 | 12.209 | 10.090 | 9.767 | A | B | B, C | C |
| IL-1α | 3.554 | 2.331 | 2.181 | 1.891 | A | A, B | B, C | C |
| IL-1β | 53.666 | 35.575 | 24.295 | 24.440 | A | B | C | C |
| TNF-β | 0.0013 | 0.0010 | 0.0008 | 0.0007 | A | B | C | C |
| IL-12p70 | 0.172 | 0.148 | 0.118 | 0.127 | A | A, B | C | B, C |
| IL-13 | 0.805 | 0.762 | 0.624 | 0.648 | A | A, B | C | B, C |
| IL-4 | 0.127 | 0.115 | 0.090 | 0.096 | A | A, B | C | B, C |
| IL-5 | 0.004 | 0.003 | 0.002 | 0.003 | A | B | C | B, C |
| CRP | 15.637 | 12.743 | 12.385 | 5.809 | A | A | A | B |
| Eotaxin | 0.077 | 0.064 | 0.059 | 0.059 | A | A, B | B | B |
| GM-CSF | 0.010 | 0.008 | 0.008 | 0.008 | A | B | B | B |
| IFNγ | 0.530 | 0.446 | 0.378 | 0.386 | A | A, B | B | B |
| IL-10 | 0.875 | 0.490 | 0.423 | 0.244 | A | A, B | B | B |
| IL-15 | 0.005 | 0.003 | 0.003 | 0.003 | A | B | B | B |
| IL-16 | 0.466 | 0.345 | 0.342 | 0.295 | A | B | B | B |
| IL-6 | 0.196 | 0.192 | 0.168 | 0.150 | A | A | A, B | B |
| IL-7 | 0.004 | 0.003 | 0.003 | 0.003 | A | B | B | B |
| IL-8 | 856.276 | 652.066 | 567.361 | 572.602 | A | B | B | B |
| MCP-1 | 0.053 | 0.047 | 0.039 | 0.039 | A | A, B | B | B |
| MDC | 0.399 | 0.407 | 0.345 | 0.339 | A | A | B | B |
| SAA | 7.039 | 6.905 | 6.092 | 5.162 | A | A | A, B | B |
| Tie-2 | 0.273 | 0.239 | 0.267 | 0.221 | A | A, B | A | B |
| VCAM-1 | 4.971 | 3.706 | 3.156 | 2.892 | A | B | B | B |
| VEGF | 0.625 | 0.511 | 0.478 | 0.480 | A | B | B | B |
| VEGF 2 | 0.772 | 0.661 | 0.620 | 0.582 | A | B | B | B |
| VEGF-D | 0.057 | 0.052 | 0.051 | 0.045 | A | A, B | A, B | B |
| VEGF-C | 0.145 | 0.149 | 0.125 | 0.137 | A, B | A | B | A, B |
| TARC | 0.020 | 0.029 | 0.019 | 0.019 | A | B | A | A |
| bFGF | 0.020 | 0.015 | 0.012 | 0.013 | A | A | A | A |
| Eotaxin-3 | 0.095 | 0.108 | 0.091 | 0.094 | A | A | A | A |
| Flt-1 | 0.390 | 0.518 | 0.433 | 0.415 | A | B | A, B | A |
| IL-12p40 | 0.039 | 0.031 | 0.028 | 0.031 | A | A | A | A |
| IL-2 | 0.166 | 0.199 | 0.210 | 0.162 | A | A | A | A |
| IL-8 (HA) | 47.508 | 44.362 | 41.260 | 39.119 | A | A | A | A |
| IP-10 | 0.540 | 1.688 | 0.740 | 0.606 | A | A | A | A |
| MCP-4 | 0.023 | 0.023 | 0.020 | 0.022 | A | A | A | A |
| MIP-1α | 0.091 | 0.091 | 0.084 | 0.080 | A | A | A | A |
| MIP-1β | 0.091 | 0.100 | 0.110 | 0.094 | A | A | A | A |
| TNFα | 2.009 | 2.067 | 2.021 | 1.670 | A | A | A | A |

Example 4—One Hundred Seventy Metabolites were Identified in Gingival Samples

The same gingival-brush samples as described in EXAMPLE 3 were used for metabonomic analyses. Fourteen volunteers were selected randomly from treatment or control regimen (Test regimen: Crest® Pro-Health Clinical Plaque Control (0.454% stannous fluoride) dentifrice, Oral-B® Professional Care 1000 with Precision Clean brush head and Crest® Pro-Health Refreshing Clean Mint (0.07% CPC) mouth rinse; Control regimen (negative control): Crest® Cavity Protection (0.243% sodium fluoride) dentifrice and Oral-B® Indicator Soft Manual toothbrush), to determine if any metabolite concentrations were changed in gingival samples during the first 3 weeks of treatment. Both baseline and week 3 samples were sent in dry ice to Metabolon, Inc. (Durham, N.C.) for metabonomic measurement. 170 metabolites were identified and quantified. As shown in TABLE 2, some metabolite concentrations were changed during the first 3 weeks of treatment. Citrulline concentrations in the gingival samples were reduced after 3 weeks of treatment in the treatment regimen group. Similarly, ornithine was also reduced in the treatment regimen group after 3 weeks of treatment. Reduction of citrulline and ornithine was likely associated with alleviation of gingivitis as citrulline was reported to be associated with endotoxin treatment (Tannahill GM1, Curtis A M, Adamik J, Palsson-McDermott E M, McGettrick A F, Goel G, Frezza C, Bernard N J, Kelly B, Foley N H, Zheng L, Gardet A, Tong Z, Jany S S, Corr S C, Haneklaus M, Caffrey B E, Pierce K, Walmsley S, Beasley F C, Cummins E, Nizet V, Whyte M, Taylor C T, Lin H, Masters S L, Gottlieb E, Kelly V P, Clish C, Auron P E, Xavier R J, O'Neill L A. Succinate is an inflammatory signal that induces IL-1β through HIF-1α. Nature. 2013 Apr. 11; 496(7444):238-42. doi: 10.1038/nature11986. Epub 2013 Mar. 24.). As shown in TABLE 2, deoxycarnitine was higher in gingivitis (baseline), indicative of abnormal β-oxidation of fatty acid. Succinate is an intermediate in the citric acid cycle. Succinate (which is an intermediate in the citric acid cycle) levels increased in gingivitis, as shown in TABLE 2.

TABLE 2

Comparison of metabolites in gingival brush samples between baseline and week 3 during gingivitis treatment

| Biochemical Name | Baseline mean | 3 week mean | 3 week/baseline | p-value | q-value | Mass |
|---|---|---|---|---|---|---|
| 13-HODE + 9-HODE | 1.0877 | 0.7088 | 0.65 | 0.0601 | 0.1338 | 295.2 |
| 1-arachidonoyl-glycerophosphoethanolamine | 1.2294 | 0.8274 | 0.67 | 0.038 | 0.1035 | 500.3 |
| 1-oleoylglycerophosphoethanolamine | 0.7378 | 1.0747 | 1.46 | 0.0767 | 0.1548 | 478.3 |
| 2-methylbutyrylcarnitine (C5) | 1.7769 | 0.6997 | 0.39 | 0.0034 | 0.0546 | 246.1 |
| adenosine 5'-monophosphate (AMP) | 1.4092 | 0.8451 | 0.6 | 0.0295 | 0.0956 | 348.1 |
| alanine | 0.8721 | 1.102 | 1.26 | 0.0318 | 0.0973 | 115.9 |
| arginylleucine | 1.4447 | 0.6819 | 0.47 | 0.0084 | 0.0777 | 288.3 |
| arginylphenylalanine | 0.9616 | 0.3335 | 0.35 | 0.0119 | 0.0777 | 322.2 |
| asparagylleucine | 0.9295 | 0.6122 | 0.66 | 0.0698 | 0.1465 | 246.2 |
| citrulline | 1.0147 | 0.71 | 0.7 | 0.0104 | 0.0777 | 176.1 |
| deoxycarnitine | 3.2381 | 0.6088 | 0.19 | 0.0003 | 0.0168 | 146.1 |
| EDTA | 1.5985 | 0.8384 | 0.52 | 0.0138 | 0.0777 | 291.1 |
| erythritol | 1.625 | 0.8085 | 0.5 | 0.0582 | 0.1325 | 217 |
| fructose | 1.9933 | 1.1106 | 0.56 | 0.0847 | 0.1605 | 217 |
| glutamine | 1.2459 | 0.8366 | 0.67 | 0.0374 | 0.1035 | 147.2 |
| glutathione, oxidized (GSSG) | 1.0161 | 1.4669 | 1.44 | 0.087 | 0.1605 | 613.1 |
| glycerol | 1.3783 | 0.8308 | 0.6 | 0.0391 | 0.1035 | 205 |
| lauryl sulfate | 1.685 | 0.8623 | 0.51 | 0.0397 | 0.1035 | 265.2 |
| leucine | 1.2158 | 0.9359 | 0.77 | 0.0613 | 0.1338 | 132.2 |
| leucylleucine | 0.9505 | 0.4393 | 0.46 | 0.0251 | 0.0877 | 245.1 |
| lysylleucine | 1.2009 | 0.5275 | 0.44 | 0.0036 | 0.0546 | 260.2 |
| lysylphenylalanine | 1.1682 | 0.4563 | 0.39 | 0.0095 | 0.0777 | 294.3 |
| maltose | 0.8727 | 1.4481 | 1.66 | 0.022 | 0.0877 | 204.1 |
| maltotriose | 1.0456 | 1.8347 | 1.75 | 0.0858 | 0.1605 | 204 |
| mannitol | 1.3004 | 0.7982 | 0.61 | 0.042 | 0.107 | 319.1 |
| ornithine | 1.2916 | 0.7069 | 0.55 | 0.0367 | 0.1035 | 141.9 |
| palatinitol | 1.4395 | 0.8272 | 0.57 | 0.0782 | 0.1549 | 204 |
| phosphate | 1.4008 | 0.8376 | 0.6 | 0.0208 | 0.0877 | 298.9 |
| proline | 1.405 | 0.99 | 0.7 | 0.0033 | 0.0546 | 116.1 |
| propionylcarnitine | 1.2565 | 0.7688 | 0.61 | 0.0201 | 0.0877 | 218.2 |
| pyroglutamine | 1.3424 | 0.7873 | 0.59 | 0.0136 | 0.0777 | 129.2 |
| serylisoleucine | 1.1753 | 0.7169 | 0.61 | 0.0814 | 0.1583 | 219.2 |
| spermidine | 1.1613 | 0.8678 | 0.75 | 0.0687 | 0.1465 | 146.2 |
| succinate | 1.2929 | 0.8113 | 0.63 | 0.0754 | 0.1548 | 247 |
| threonylleucine | 1.1513 | 0.4931 | 0.43 | 0.0044 | 0.0594 | 231.2 |
| threonylphenylalanine | 1.7693 | 0.918 | 0.52 | 0.0233 | 0.0877 | 267.2 |
| trehalose | 2.3563 | 0.9084 | 0.39 | 0.0054 | 0.0647 | 361.2 |
| tryptophan | 1.1518 | 0.9089 | 0.79 | 0.0487 | 0.1185 | 205.1 |
| tyrosine | 1.383 | 1.0299 | 0.74 | 0.0161 | 0.0787 | 182.1 |
| valine | 1.1598 | 0.9271 | 0.8 | 0.0304 | 0.0956 | 118.1 |
| valylvaline | 0.9347 | 0.8231 | 0.88 | 0.0508 | 0.1207 | 215.2 |
| X-13671 | 0.5035 | 0.918 | 1.82 | 0.0545 | 0.1267 | 315.3 |
| X-14588 | 1.3647 | 0.8378 | 0.61 | 0.024 | 0.0877 | 151 |
| X-16103 | 1.3643 | 0.8461 | 0.62 | 0.0297 | 0.0956 | 99.3 |
| X-17266 | 1.3158 | 0.576 | 0.44 | 0.0003 | 0.0168 | 530.4 |
| X-17375 | 1.4785 | 0.8387 | 0.57 | 0.0189 | 0.0877 | 357.1 |
| X-18472 | 0.6138 | 1.1441 | 1.86 | 0.0011 | 0.0405 | 827.1 |
| X-18779 | 1.3756 | 0.8035 | 0.58 | 0.0162 | 0.0787 | 209.1 |
| X-19607 | 1.5237 | 0.7167 | 0.47 | 0.002 | 0.0537 | 366.1 |
| X-19609 | 1.3284 | 0.7721 | 0.58 | 0.016 | 0.0787 | 204 |
| X-19612 | 1.3896 | 0.7843 | 0.56 | 0.01 | 0.0777 | 427.2 |
| X-19613 | 1.3412 | 0.7535 | 0.56 | 0.0099 | 0.0777 | 429.3 |
| X-19614 | 1.3378 | 0.7343 | 0.55 | 0.0454 | 0.113 | 570.1 |
| X-19807 | 1.3478 | 0.8411 | 0.62 | 0.0244 | 0.0877 | 93 |
| X-19808 | 1.3348 | 0.8368 | 0.63 | 0.0254 | 0.0877 | 95 |
| X-19850 | 1.3576 | 0.7519 | 0.55 | 0.011 | 0.0777 | 334.2 |
| X-19857 | 1.3357 | 0.8032 | 0.6 | 0.038 | 0.1035 | 230 |
| X-20000 | 1.2784 | 0.7536 | 0.59 | 0.0133 | 0.0777 | 81.2 |

Example 5—Citrulline was Reduced in Regiment Treatment Over 6 Weeks

Quantitation of citrulline and ornithine from the extracts of the same Gingival-brush samples as described in EXAMPLE 2, was conducted using gradient hydrophilic interaction liquid chromatography with tandem mass spectrometry (HILIC/MS/MS). The gingival-brush samples were placed into extraction buffer as described in EXAMPLE 1. The supernatants were subject to both HILIC/MS/MS and BCA analysis. For free citrulline and ornithine analysis, the extracts of the Gingival-brush samples were analyzed either directly (50 μl of gingival brush extract with 50 μl sample solution sample solution (50/50 acetonitrile/ultra-pure water with 0.754% formic acid) or diluted 5 fold with sample solution. For total citrulline and ornithine analysis, the extracts of the Gingival-brush samples were first hydrolyzed using 6 N HCl (50 μL of extract with 450 μL of 6N HCl), no shaking, and placed on a hot plate at 110° C. for 16 hours. The hydrolyzed samples were then dried down under vacuum at room temperature (Savant speedvac of Lifetechnology, Grand Island, N.Y.) and then reconstituted in 1 ml of dilution solution (50/50 acetonitrile/ultra-pure water with 0.754% formic acid) for analysis. The standards and the samples were analyzed using gradient hydrophilic interaction liquid chromatography with tandem mass spectrometry (HILIC/MS/MS). Analytes and the corresponding ISTDs (stable isotope labeled internal standard) were monitored by electrospray ionization (ESI) in positive mode using the selected-reaction-monitoring schemes shown in TABLE 3. A standard curve was constructed by plotting the signal, defined here as the peak area ratio (peak area analyte/peak area ISTD), for each standard versus the mass of each analyte for the corresponding standard. The mass of each analyte in the calibration standards and Gingival-brush extract samples were then back-calculated using the generated regression equation. The concentration of protein bound citrulline or ornithine was calculated as the result of subtracting the concentration of free citrulline or ornithine from the concentration of total citrulline or ornithine, respectively. As shown in TABLE 3, the result was reported as the concentration of citrulline or ornithine or the result was standardized by dividing by the amount of citrulline or ornithine by the amount of the total proteins that were found in the extract.

TABLE 3

Multiple Reaction Monitoring (MRM) transitions for analytes and their corresponding stable isotope labeled internal standards

| Analytes | MRM | Internal Standards | MRM |
| --- | --- | --- | --- |
| Citrulline | 176 → 159 | $d_7$-Citrulline | 181 → 164 |
| Ornithine | 133 → 70 | $d_6$-Ornithine | 139 → 76 |

Figure 5:
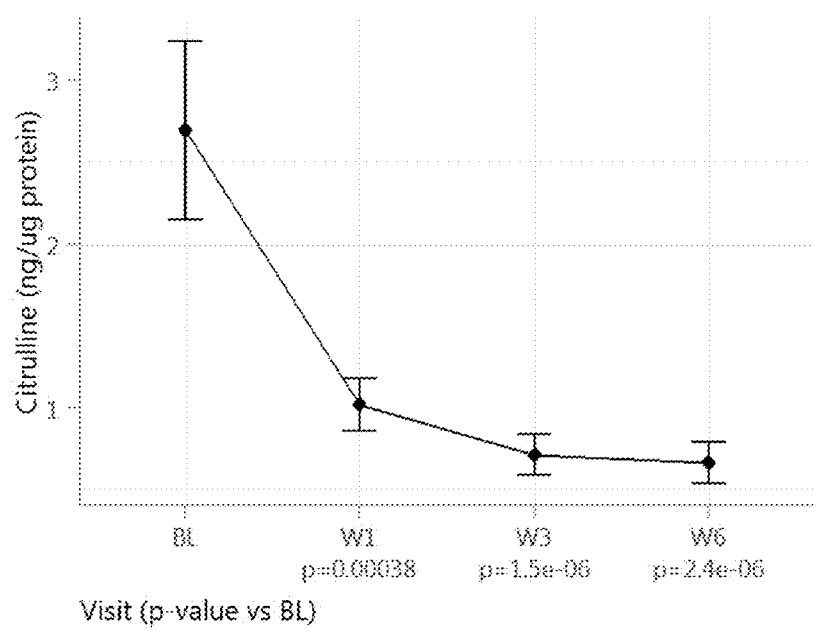
FIG. 5 is a line graph showing decreasing citrulline concentrations in Buccal-brush samples.

All samples in the regimen treatment, as described in EXAMPLE 2, were analyzed. As shown in FIG. 5, citrulline levels reduced rapidly in the first week of treatment, and then continued to decline gradually in weeks 3 and 6 of treatment. These results are consistent with clinical observations, where gingival bleeding sites (GBI) and the gingival inflammation (MGI) were reduced over the 6-week treatment period.

Example 6—Levels of Proteins Containing Ornithine Decreased Over 6 Week Treatment The same gingival-brush samples were collected using the procedures described in EXAMPLE 1, from the same volunteers as in EXAMPLE 2. Before sampling, volunteers rinsed their mouths for 30 seconds with water. A dental hygienist then sampled the area just above the gumline using a buccal swab brush (Epicentre Biotechnologies, Madison, Wis., cat. #MB100SP). The swab was immediately placed into 1 ml extraction buffer [PBS, 0.25M NaCl, 1× Halt™ Protease Inhibitor Single-Use Cocktail (Lifetechnologies, Grand Island, N.Y.)] in a 1.5 ml Eppendorf tube vortexed for 30 seconds, and immediately frozen on dry ice and stored in a −80 C freezer until analysis. The samples were taken out of the freezer, thawed and extracted by placing the samples on a tube shaker for 30 minutes at 4° C. The tubes were centrifuged at 15000 RPM for 10 min in Eppendorf Centrifuge 5417R (Eppendorf, Ontario, Canada) to pellet any debris. The extract (800 µl) was analyzed for protein concentrations using the Bio-Rad protein assay (BioRad, Hercules, Calif.). Subjects with gingivitis followed test regimen for 6 weeks (Crest® Pro-Health Clinical Plaque Control (0.454% stannous fluoride) dentifrice, Oral-B® Professional Care 1000 with Precision Clean brush head and Crest® Pro-Health Refreshing Clean Mint (0.07% CPC) mouth rinse). Baseline (BL) represents diseased status. Symptoms of gingivitis, such as bleeding and inflammation were alleviated at week 1 to week 6 treatments. Protein bound ornithine (the difference between total and the free ornithine) was higher in gingivitis as shown in FIG. 6. Protein bound ornithine was reduced gradually as gingivitis was decreased in severity.

Example 7—Expression of Enzymes in the Ornithine-Citrulline-Arginine Cycle was Changed in Gingival Samples During the 6 Week Treatment Separate gingival samples were collected as described in EXAMPLES 1 and 3, from the same volunteers as in EXAMPLE 2, and were used to examine the expression of genes during 6 weeks of treatment. After harvesting the samples, the brush was completely immersed in RNAlater solution (1 ml in a 1.5 ml Eppendorf tube) to prevent RNA degradation during transport and storage (Qiagen, Valencia, Calif.). The vials were vortexed/mixed for 30 seconds, immediately frozen on dry ice, stored and transferred on dry ice to the lab for biomarker analysis. RNA isolation and microarray analysis were performed as described previously in a publication (Offenbacher S, Barros S P, Paquette D W, Winston J L, Biesbrock A R, Thomason R G, Gibb R D, Fulmer A W, Tiesman J P, Juhlin K D, Wang S L, Reichling T D, Chen K S, Ho B. J Periodontol. 2009 December; 80(12):1963-82. doi: 10.1902/jop.2009.080645. Gingival transcriptome patterns during induction and resolution of experimental gingivitis in humans).

Figure 7:
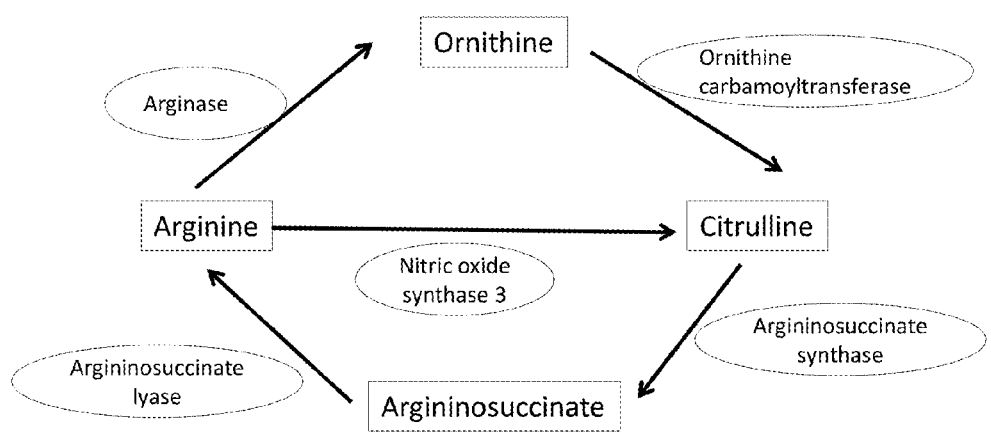
FIG. 7 shows a drawing outlining the enzymes in the ornithine, citrulline and arginine cycle.

The ornithine-citrulline-arginine cycle consists of four enzymes (FIG. 7). The main feature of the cycle is that three amino acids can be converted to each other. The first enzyme is ornithine carbmoyltranferase, which transfers a carbamoyl group from carbamoyl phosphate to ornithine to generate citrulline. This reaction occurs in the matrix of the mitochondria. Expression of ornithine carbmoyltranferase was reduced in the treatment (FIG. 8). The second enzyme is argininosuccinate synthase. This enzyme uses ATP to activate citrulline by forming a citrullyl-AMP intermediate, which is attacked by the amino group of an aspartate residue to generate argininosuccinate. This reaction and the subsequent two reactions (argininosuccinate to arginine and arginine to ornithine) occur in cytosol. Again, expression of argininosuccinate synthetase decreased during the treatment. The third enzyme is argininosuccinate lyase, which catalyzes cleavage of argininosuccinate into fumarate and arginine. The last enzyme is argininase. Argininases cleave arginine to produce urea and ornithine. In a contrast to the decreased expression of both ornithine carbmoyltranferase and argininosuccinate synthetase genes, argininase I (liver) and II increased (FIG. 8).

Arginine is also a substrate for nitric oxide synthases, which oxidizes arginine to produce citrulline and nitric oxide. Expression of nitric oxide synthase 3 gene increased too (FIG. 8).

Example 8—Citrulline Increased in Gingival Samples in Experiment Gingivitis

Experimental gingivitis: Another clinical study was carried out to determine whether citrulline is increased in experimentally induced gingivitis in healthy human volunteers. This was a case-control study enrolling 60 volunteers. The study population included two groups as follows: Group 1 or high bleeders group, thirty (30) volunteers with at least 20 bleeding sites, where bleeding is a GBI site score of 1 or 2 at baseline. Group 2, or low bleeders group, thirty (30) volunteers with 2 or less bleeding sites, where bleeding is a GBI site score of 1 or 2.

The study consisted of two Phases: Health/Rigorous Hygiene Phase with a dental cleaning procedure to thoroughly clean the teeth, polishing and rigorous oral hygiene; and induced gingivitis phase without oral hygiene. At the Screening visit, volunteers underwent an oral soft tissue assessment and had a gingivitis evaluation (Modified Gingival Index (MGI) and Gingival Bleeding Index (GBI). At Visit 2 (following the screening visit) participants received an oral soft tissue exam followed by a gingivitis evaluation, and gingival samples were collected, as described below, for host biomarker analysis. Following that, all volunteers entered the Health/Rigorous Hygiene Phase, lasting two weeks. After two weeks of rigorous hygiene, all volunteers entered the Induced Gingivitis Phase, lasting for three weeks. Oral soft tissue exams and gingivitis were re-evaluated and all gingival samples were collected at Baseline, WK0 and WK2.

Gingival sample collection—A gingival brush sample was collected from each side of the upper arch using the procedures as described in EXAMPLE 1. Gingival brush samples were collected close to the gumline from the buccal sites only (preferably from four adjacent teeth—preferably from premolar and molar areas). Volunteers rinsed for 30 seconds with 15 ml of Listerine rinse to clean the surface of sampling area. After the Listerine rinse, volunteers rinsed for 30 seconds with 20 ml of water. Following that, selected sites were isolated with a cotton roll and gently dried with an air syringe and two gum swabs were taken with collection brushes/swabs from the gingiva region close to the gumline of the selected teeth. The samples were placed in a pre-labeled (volunteer ID, sample ID, visit, and date) vial containing 1 ml extraction buffer [PBS, 0.25M NaCl, 1× Halt™ Protease Inhibitor Single-Use Cocktail (Life Technologies, Grand Island, N.Y.)] in a 1.5 ml Eppendorf tube. The vials were vortexed/mixed for 30 seconds, immediately frozen on dry ice, stored and transferred on dry ice to the lab for biomarker analysis. Samples from three visits were analyzed using the procedures as described as in EXAMPLE 5, and shown in FIG. 9. Those three visits were baseline, Week 0, (right after the Health/Rigorous Hygiene Phase and before the induced gingivitis phase) and week 2 (at the end of Induced Gingivitis Phase). Free citrulline levels were low in both the high and low bleeders groups at the baseline and week 0, but rose quickly in the induced gingivitis in both groups at week 2.

Example 9—Levels of Proteins Containing Citrulline Decreased in Experimentally Induced Gingivitis The same procedures were used as described in EXAMPLE 5. The samples were the same as described in EXAMPLE 8. Protein bound citrulline was lower at the baseline than that at week 0 in both high and low bleeders groups, as shown in FIG. 10 in gingival tissue. It was low in experimental gingivitis in both groups at week 2.

Example 10—Levels of Proteins Containing Ornithine Increased in Gingival Samples in Experiment Gingivitis The same gingival brush samples from experimental gingivitis, as described in EXAMPLE 8 were analyzed using the procedures described in EXAMPLE 5. The bound ornithine was the lowest at week 0 (FIG. 11) in both groups. Its levels at the baseline were higher than those at week 0. The bound ornithine reached peaks when gingivitis was induced in both groups at week 2. Also it is worth noting the total ornithine (Free and protein bound ornithine) was increased in the induced gingivitis (FIG. 12) in both groups.

Example 11

Levels of Proteins Containing Arginine Decreased in Gingival Samples in Experimentally Induced Gingivitis The same gingival brush samples from experimental gingivitis, as described in EXAMPLE 8 were analyzed using the procedures as described in EXAMPLE 5. The protein bound arginine was the lowest in induced gingivitis (FIG. 13) in both groups. Its levels were higher in WK0 than that at baseline in both groups. The total arginine in the gingival brush samples displayed the same patterns as the protein bound one (FIG. 14).

Example 12—Human Dental Plaques, Lipopolysaccharides (LPS) and Lipoteichoic Acids (LTA) Stimulated Production of Citrulline, Ornithine, Arginine, Malic Acid, Fumaric Acid and Succinic Acid Human primary blood mononuclear cells were isolated from blood obtained from Gulf Coast Regional Blood Center, Houston, Tex., USA, using Histopaque 1077 (Sigma Aldrich Co., St. Louis, Mo.) and Leucosep tubes (Greiner Bio-One, Monroe, N.C.). The cells were cultured in 200 μl of Roswell Park Memorial Institute (RPMI) 1640 medium in each well of a 90-well plate (ThermoFisher Scientific, Inc., Grand Island, N.Y.) containing 10% fetal bovine serum and 1% penicillin/streptomycin antibiotics at 37° C. with a 5% $CO_2$ atmosphere. *B. subtilis* LTA, *S. aureus* LTA, *P. gingivalis* LPS and *E. coli* LPS were purchased from Invivogen (San Diego, Calif.). Human dental plaques were harvested in a controlled clinical examiner-blind study. Forty (40) volunteers were used, twenty (20) of which were qualified as healthy—each having up to 3 bleeding sites and with all pockets less than or equal to 2 mm deep; and twenty (20) volunteers were qualified as unhealthy—greater than 20 bleeding sites with at least 3 pockets greater than or equal to 3 mm but not deeper than 4 mm with bleeding, and at least 3 pockets less than or equal to 2 mm deep with no bleeding for sampling. Volunteers had up to 6 sites identified as "sampling sites". "Sampling sites" had supragingival and subgingival plaque collected at Baseline, Week 2 and Week 4. Subgingival plaque samples were taken from a gingival sulcus from the pre-identified sites. Prior to sample collection, the site had supragingival plaque removed with a curette. The site was dried and subgingival plaque sample were collected with another dental curette (e.g., Gracey 13/14, 15/16, 11/12, 7/8, 1/2). Samples from each site were placed in a pre-labeled 2.0 ml sterile tube containing 300 μl DPBS buffer with about 30 glass beads of 1 mM in diameter. Samples were stored at 4° C. and shipped overnight at 4° C. The subgingival samples were stored at −80° C. freezer until being analyzed. The samples were thawed and dispersed in a TissueLyser II (Qiagen, Valencia, Calif., USA) at 30 shakes per second for 3 min. Protein concentrations of the dispersed subgingival samples were measured using a Pierce microBCA Protein kit (ThermoFisher Scientific, Grand Island, N.Y., USA) following the manufacturer's instruction.

The cells were seeded onto 96-well at 100,000 cells per well in 200 μl of RPMI 1640 medium in each well (ThermoFisher Scientific, Inc., Grand Island, N.Y., USA) containing 10% fetal bovine serum and 1% penicillin/streptomycin antibiotics, and treated with clinical samples and bacterial components. The cells were then incubated for 24 hours at 37° C. with a 5% $CO_2$ atmosphere. Cells were harvested with medium into a 15 ml polypropylene conical tube at the end of experiment. Cells were separated from medium by centrifugation at 1000 RPM for 10 min at 4° C., and immediately frozen and stored at −80° C. until analysis. The samples were analyzed using the procedures as described in EXAMPLE 5.

The human subgingival plaques were pooled from 60 subgingival plaques of bleeding sites. The pooled samples stimulated production of citrulline, arginine and ornithine in primary human peripheral blood mononuclear cells (TABLE 4). Similarly, they also increased malic acid, fumaric acid and succinic acid in the same cells. LPS and LTA also increased production of citrulline, ornithine, arginine and succinic acid in the human primary peripheral blood cells.

bacher S, Barros S P, Paquette D W, Winston J L, Biesbrock A R, Thomason R G, Gibb R D, Fulmer A W, Tiesman J P, Juhlin K D, Wang S L, Reichling T D, Chen K S, Ho B. J Periodontol. 2009 December; 80(12):1963-82. doi: 10.1902/jop.2009.080645. Gingival transcriptome patterns during induction and resolution of experimental gingivitis in humans).

Claudins are a family of proteins that are the most important components of the tight junctions, where they establish the paracellular barrier that controls the flow of molecules in the intercellular space between the cells of an epithelium. They have four transmembrane domains, with the N-terminus and the C-terminus in the cytoplasm. Similar

TABLE 4

Human subgingival plaques, LPS and LTA increased production of citrulline, ornithine, arginine and succinic acid in human primary peripheral blood mononuclear cells.

| Sample Treatment | Treatment Dose ng/ml | Arginine ng/ml | Citrulline ng/ml | Ornithine ng/ml | Malic Acid ng/ml | Fumaric Acid ng/ml | Succinic Acid ng/ml |
|---|---|---|---|---|---|---|---|
| LPS-*E. coli* | 900 ng/ml | 28100 | 408 | 2697 | 565 | 116 | 1140 |
| LPS-*P. gingivalis* | 100 ng/ml | 42931 | 271 | 4367 | 650 | 129 | 1740 |
| LTA-*S. aureus* | 900 ng/ml | 38919 | 544 | 4145 | 628 | 137 | 1290 |
| LTA-*B. subtilis* | 900 ng/ml | 35415 | 303 | 4200 | 788 | 179 | 1300 |
| human subgingival plaques | 19 ng/ml proteins | 59279 | 539 | 7580 | 919 | 202 | 2530 |
| Cells Only | Culture medium | 23733 | 121 | 2394 | 559 | 127 | 825 |

Example 13—Expression of Genes Whose Products Strengthen Barrier Functions in Gingivae Separate gingival samples were collected as described in EXAMPLES 1 and 3, from the same volunteers as in EXAMPLE 2, and were used to examine the expression of genes during the six week treatment. After harvesting the samples, the brush was completely immersed in the RNAlater solution to prevent RNA degradation during transport and storage (Qiagen, Valencia, Calif.). The vials were vortexed/mixed for 30 seconds, immediately frozen on dry ice, stored and transferred on dry ice to the lab for biomarker analysis. RNA isolation and microarray analysis were performed as described previously in a publication (Offento keratins, different claudins are expressed in different layers of keratincoytes during differentiation. Claudins are important components in barrier functions. As shown in TABLE 5, CLDN 1 and 12 decreased during the treatment while CLDN17 and 23 increased. Those changes can be explored as biomarkers in gingivitis.

TABLE 5

Expression of genes for claudins in gingival brush samples during treatment of gingivitis at baseline, weeks 1, 3 and 6.

| gene_name | probe_id | symbol | Group means (log2) | | | | Group change from Baseline P-values (Surrogate Variable Analysis) | | |
|---|---|---|---|---|---|---|---|---|---|
| | | | Baseline | Week 1 | Week 3 | Week 6 | Week 1 | Week 3 | Week 6 |
| claudin 1 | 11728234_a_at | CLDN1 | 6.94 | 6.53 | 6.46 | 6.30 | 0.00 | 0.00 | 0.00 |
| claudin 12 | 11720206_s_at | CLDN12 | 6.43 | 6.27 | 6.26 | 6.22 | 0.01 | 0.00 | 0.00 |
| claudin 17 | 11738572_at | CLDN17 | 7.42 | 8.10 | 8.27 | 8.10 | 0.00 | 0.00 | 0.00 |
| claudin 23 | 11728603_a_at | CLDN23 | 7.26 | 7.52 | 7.56 | 7.58 | 0.00 | 0.00 | 0.00 |

Peptidylarginine deiminases catalyze a form of post translational modification called arginine de-imination or citrullination. These family members have distinct substrate specificities and tissue-specific expression patterns. Peptidyl arginine deiminase, type I, also known as PADI1 is involved in the late stages of epidermal differentiation, where it deiminates filaggrin and keratin K1, which maintains hydration of the stratum corneum, and hence the cutaneous barrier function. PADI2 is widely expressed. Its known substrates for PADI2 include myelin basic protein in the central nervous system and vimentin in skeletal muscle and macrophages. PADI3 is involved in both hair and skin differentiation. As shown in TABLE 6, PADI1 increased while PADI2 decreased during the treatment periods. Those changes can be used as biomarkers of gingivitis severity.

TABLE 6

Expression of genes for peptidylarginine deiminases in gingival brush samples during treatment of gingivitis at baseline, weeks 1, 3 and 6.

| gene_name | probe_id | symbol | Group means (log2) | | | | Group change from Baseline P-values (Surrogate Variable Analysis) | | |
|---|---|---|---|---|---|---|---|---|---|
| | | | Baseline | Week 1 | Week 3 | Week 6 | Week 1 | Week 3 | Week 6 |
| peptidyl arginine deiminase, type I | 11751221_a_at | PADI1 | 8.72 | 8.80 | 9.02 | 9.05 | 0.000 | 0.000 | 0.000 |
| peptidyl arginine deiminase, type I | 11751731_a_at | PADI1 | 7.55 | 7.71 | 7.90 | 7.92 | 0.001 | 0.000 | 0.000 |
| peptidyl arginine deiminase, type I | 11729333_at | PADI1 | 10.17 | 10.13 | 10.32 | 10.37 | 0.002 | 0.000 | 0.003 |
| peptidyl arginine deiminase, type II | 11727597_at | PADI2 | 6.98 | 6.74 | 6.61 | 6.51 | 0.008 | 0.000 | 0.000 |
| peptidyl arginine deiminase, type II | 11745141_a_at | PADI2 | 6.61 | 6.55 | 6.57 | 6.55 | 0.011 | 0.027 | 0.003 |
| peptidyl arginine deiminase, type III | 11736978_at | PADI3 | 6.67 | 6.73 | 6.91 | 6.87 | 0.005 | 0.001 | 0.000 |
| peptidyl arginine deiminase, type VI | 11741173_at | PADI6 | 4.54 | 4.52 | 4.51 | 4.53 | 0.010 | 0.008 | 0.219 |

Keratin is a family of fibrous structural proteins, the key structural material making up the outer layer of human skin, oral mucosa and gingivae. Keratins provide the necessary strength and barrier functions. Keratin monomers assemble into bundles to form intermediate filaments. Keratin compositions change in keratinocytes when they move outward from stratum basale, to spinosum, granulosum and corneum. As shown in TABLE 7, expression of keratin genes changed significantly during the treatment period. Those changes can be used as biomarkers of gingivitis severity.

TABLE 7

Expression of genes for keratins in gingival brush samples during treatment of gingivitis at baseline, weeks 1, 3 and 6.

| gene_name | probe_id | symbol | Group means (log2) | | | | Group change from Baseline P-values (Surrogate Variable Analysis) | | |
|---|---|---|---|---|---|---|---|---|---|
| | | | Baseline | Week 1 | Week 3 | Week 6 | Week 1 | Week 3 | Week 6 |
| keratin 13 | 11747755_a_at | KRT13 | 11.72 | 11.93 | 11.94 | 11.94 | 0.00 | 0.00 | 0.00 |
| keratin 15 | 11728288_a_at | KRT15 | 9.17 | 8.85 | 8.77 | 8.71 | 0.09 | 0.00 | 0.00 |
| keratin 18 | 11757905_x_at | KRT18 | 8.18 | 8.57 | 8.70 | 8.70 | 0.00 | 0.00 | 0.00 |
| keratin 31 | 11731269_at | KRT31 | 5.40 | 5.52 | 5.61 | 5.61 | 0.16 | 0.00 | 0.00 |
| keratin 4 | 11739440_a_at | KRT4 | 10.98 | 11.39 | 11.48 | 11.57 | 0.00 | 0.00 | 0.00 |
| keratin 6A | 11747769_x_at | KRT6A | 10.05 | 10.38 | 10.27 | 10.25 | 0.02 | 0.05 | 0.14 |
| keratin 6B | 11723983_at | KRT6B | 7.80 | 8.36 | 8.24 | 8.11 | 0.01 | 0.00 | 0.09 |
| keratin 6C | 11727492_at | KRT6C | 7.87 | 8.54 | 8.23 | 8.13 | 0.00 | 0.05 | 0.25 |
| keratin 7 | 11715683_a_at | KRT7 | 6.48 | 6.23 | 6.23 | 5.89 | 0.14 | 0.00 | 0.00 |
| keratin 80 | 11728960_a_at | KRT80 | 7.92 | 8.11 | 8.20 | 8.13 | 0.00 | 0.00 | 0.00 |

To provide protection against external environment and microbial, gingival keratinocytes undergo differentiation. Expression of differentiation genes, such as involucrin, loricrin, filaggrin, envoplakin and periplakin genes, are elevated as keratinocytes migrate outward from stratum basale to corneum. As shown in TABLE 8, expression of those differentiation genes was elevated during treatment. The increased expression of keratinocyte differentiation genes can be used as biomarkers of gingivitis severity.

TABLE 8

Expression of genes for keratinocyte differentiation in gingival brush samples during treatment of gingivitis at baseline, weeks 1, 3 and 6.

| gene_name | probe_id | symbol | Group means | | | | Group change from Baseline P-values (Surrogate Variable Analysis) | | |
|---|---|---|---|---|---|---|---|---|---|
| | | | Baseline | Week 1 | Week 3 | Week 6 | Week 1 | Week 3 | Week 6 |
| envoplakin | 11726123_a_at | EVPL | 7.61 | 8.03 | 8.12 | 8.15 | 0.00 | 0.00 | 0.00 |
| filaggrin | 11741116_at | FLG | 9.13 | 9.45 | 9.48 | 9.49 | 0.00 | 0.00 | 0.00 |
| involucrin | 11731653_a_at | IVL | 8.81 | 9.36 | 9.55 | 9.55 | 0.00 | 0.00 | 0.00 |
| loricrin | 11731852_at | LOR | 5.95 | 6.36 | 6.33 | 6.63 | 0.12 | 0.11 | 0.01 |
| periplakin | 11722429_s_at | PPL | 8.32 | 8.79 | 8.86 | 8.85 | 0.00 | 0.00 | 0.00 |
| periplakin | 11750591_a_at | PPL | 7.19 | 7.68 | 7.79 | 7.78 | 0.00 | 0.00 | 0.00 |
| periplakin | 11722428_a_at | PPL | 7.59 | 8.09 | 8.16 | 8.16 | 0.00 | 0.00 | 0.00 |
| periplakin | 11722430_at | PPL | 11.27 | 11.34 | 11.43 | 11.41 | 0.00 | 0.00 | 0.00 |

Example 14—Expression of Lipoxygenases and Prostaglandin-Endoperoxide Synthesis 2 in Gingivae The same gingival samples, as described as in EXAMPLE 13, were used to examine the expression of genes during the six week treatment. After harvesting the samples, the brush was completely immersed in the RNAlater solution to prevent RNA degradation during transport and storage (Qiagen, Valencia, Calif.). The vials were vortexed/mixed for 30 seconds, immediately frozen on dry ice, stored and transferred on dry ice to the lab for biomarker analysis. RNA isolation and microarray analysis were performed as described previously in a publication (Offenbacher S, Barros S P, Paquette D W, Winston J L, Biesbrock A R, Thomason R G, Gibb R D, Fulmer A W, Tiesman J P, Juhlin K D, Wang S L, Reichling T D, Chen K S, Ho B. J Periodontol. 2009 December; 80(12):1963-82. doi: 10.1902/jop.2009.080645. Gingival transcriptome patterns during induction and resolution of experimental gingivitis in humans).

15-Lipoxygenase and 5-lipoxygenase are highly regulated lipid-peroxidating enzymes whose expression and their metabolites are implicated in several important inflammatory conditions. As shown in TABLE 9, ALOX15B, ALOX5, ALOX5AP and PTGS2 decreased during treatment. Their changes can be used as biomarkers of gingivitis severity.

Example 15—Expression of Glutathione Peroxidases in Gingivae

The same gingival samples, as described in EXAMPLE 13, were used to examine the expression of genes during the six week treatment. After harvesting the samples, a brush was completely immersed in RNAlater solution to prevent RNA degradation during transport and storage (Qiagen, Valencia, Calif.). The vials were vortexed/mixed for 30 seconds, immediately frozen on dry ice, stored and transferred on dry ice to the lab for biomarker analysis. RNA isolation and microarray analysis were performed as described previously in a publication (Offenbacher S, Banos S P, Paquette D W, Winston J L, Biesbrock A R, Thomason R G, Gibb R D, Fulmer A W, Tiesman J P, Juhlin K D, Wang S L, Reichling T D, Chen K S, Ho B. J Periodontol. 2009 December; 80(12):1963-82. doi: 10.1902/jop.2009.080645. Gingival transcriptome patterns during induction and resolution of experimental gingivitis in humans).

Glutathione peroxidase (GPX) was increased during treatment. It is an enzyme with peroxidase activity. Its main biological role is to protect the organism from oxidative damage. The biochemical function of glutathione peroxidase is to reduce lipid hydroperoxides to their corresponding alcohols and to reduce free hydrogen peroxide to water. As shown in TABLE 10, both GPX1 and GPX3 were increased during treatment. Their changes represent reduction in gingivitis severity.

TABLE 9

Expression of genes for metabolizing polyunsaturated fatty acids in gingival brush samples during treatment of gingivitis at baseline, weeks 1, 3 and 6.

| gene_name | probe_id | symbol | Group means (log2) | | | | Group change from Baseline P-values (Surrogate Variable Analysis) | | |
|---|---|---|---|---|---|---|---|---|---|
| | | | Baseline | Week 1 | Week 3 | Week 6 | Week 1 | Week 3 | Week 6 |
| arachidonate 15-lipoxygenase, type B | 11734619_x_at | ALOX15B | 6.10 | 5.73 | 5.61 | 5.66 | 0.00 | 0.00 | 0.00 |
| arachidonate 15-lipoxygenase, type B | 11752283_a_at | ALOX15B | 5.55 | 5.29 | 5.23 | 5.25 | 0.02 | 0.00 | 0.00 |
| arachidonate 5-lipoxygenase | 11726337_a_at | ALOX5 | 5.11 | 4.97 | 4.97 | 4.93 | 0.00 | 0.00 | 0.00 |
| arachidonate 5-lipoxygenase-activating protein | 11719479_at | ALOX5AP | 7.19 | 6.84 | 6.75 | 6.74 | 0.00 | 0.00 | 0.00 |
| prostaglandin-endoperoxide synthase 2 | 11724037_at | PTGS2 | 7.80 | 7.30 | 7.13 | 7.06 | 0.05 | 0.00 | 0.00 |

TABLE 10

Expression of genes for glutathione peroxidases in gingival brush samples during treatment of gingivitis at baseline, weeks 1, 3 and 6.

| | | | Group means (log2) | | | | Group change from Baseline P-values (Surrogate Variable Analysis) | | |
|---|---|---|---|---|---|---|---|---|---|
| gene_name | probe_id | symbol | Baseline | Week 1 | Week 3 | Week 6 | Week 1 | Week 3 | Week 6 |
| glutathione peroxidase 1 | 11725346_x_at | GPX1 | 6.43 | 6.76 | 6.60 | 6.56 | 0.00 | 0.00 | 0.01 |
| glutathione peroxidase 3 (plasma) | 11730170_a_at | GPX3 | 5.56 | 5.99 | 6.04 | 6.02 | 0.00 | 0.00 | 0.00 |

Example 16—Expression of Genes for the Citric Acid Cycle, β-Oxidation, and Oxidative Phosphorylation The same gingival samples were collected and analyzed as described in EXAMPLE 13. β-oxidation is the catabolic process in which chain fatty acid molecules with different lengths are cleaved in the cytosol in the mitochondria in eukaryotes to generate acetyl-CoA. The latter enters the citric acid cycle and results in production of ATP subsequently.

Many enzymes are involved in this process. As shown in TABLE 11, expression of those genes increased during treatment. Increase in their expression is indicative of the improvement in ATP production in the gingival tissue.

TABLE 11

Expression of genes for the citric acid cycle, β-oxidation, and oxidative phosphorylation in gingival brush samples during treatment of gingivitis at baseline, weeks 1, 3 and 6.

| | | | Group means (log2) | | | | Group change from Baseline P-values (Surrogate Variable | | |
|---|---|---|---|---|---|---|---|---|---|
| gene_name | probe_id | symbol | Baseline | Week 1 | Week 3 | Week 6 | Week 1 | Week 3 | Week 6 |
| acyl-CoA dehydrogenase, C-4 to C-12 straight chain | 11722357_a_at | ACADM | 7.18 | 7.52 | 7.46 | 7.45 | 0.00 | 0.00 | 0.00 |
| acyl-CoA dehydrogenase, C-4 to C-12 straight chain | 11757536_s_at | ACADM | 7.73 | 8.05 | 7.95 | 7.85 | 0.00 | 0.00 | 0.00 |
| carnitine O-octanoyltransferase | 11720743_x_at | CROT | 6.29 | 6.43 | 6.56 | 6.51 | 0.00 | 0.00 | 0.00 |
| carnitine O-octanoyltransferase | 11720744_a_at | CROT | 4.85 | 4.89 | 4.93 | 4.92 | 0.07 | 0.00 | 0.07 |
| electron-transferring-flavoprotein dehydrogenase | 11749144_s_at | ETFDH | 6.12 | 6.42 | 6.47 | 6.45 | 0.00 | 0.00 | 0.00 |
| NADPH dependent diflavin oxidoreductase 1 | 11734007_s_at | NDOR1 | 6.88 | 7.16 | 7.29 | 7.07 | 0.00 | 0.00 | 0.00 |
| NADH dehydrogenase (ubiquinone) 1 alpha subcomplex, 11, 14.7 kDa | 11716354_a_at | NDUFA11 | 7.17 | 7.41 | 7.43 | 7.33 | 0.00 | 0.00 | 0.00 |
| NADH dehydrogenase (ubiquinone) 1 alpha subcomplex, 4-like 2 | 11717202_x_at | NDUFA4L2 | 6.38 | 6.83 | 6.85 | 6.85 | 0.00 | 0.00 | 0.00 |
| NADH dehydrogenase (ubiquinone) 1 alpha subcomplex, 6, 14 kDa | 11718765_a_at | NDUFA6 | 6.43 | 6.79 | 6.86 | 6.78 | 0.00 | 0.00 | 0.00 |
| NADH dehydrogenase (ubiquinone) 1 beta subcomplex, 11, 17.3 kDa | 11717251_s_at | NDUFB11 | 8.45 | 8.89 | 8.91 | 8.86 | 0.00 | 0.00 | 0.00 |
| NADH dehydrogenase (ubiquinone) 1 beta subcomplex, 4, 15 kDa | 11745384_s_at | NDUFB4 | 7.03 | 7.38 | 7.35 | 7.27 | 0.00 | 0.00 | 0.00 |
| succinate dehydrogenase complex, subunit A, flavoprotein (Fp) | 11749757_x_at | SDHA | 7.67 | 7.94 | 8.11 | 7.99 | 0.00 | 0.00 | 0.00 |
| succinate dehydrogenase complex, subunit A, flavoprotein (Fp) | 11747868_x_at | SDHA | 7.61 | 7.91 | 7.98 | 7.97 | 0.00 | 0.00 | 0.00 |
| ubiquinol-cytochrome c reductase, complex III subunit X | 11757670_a_at | UQCR10 | 6.43 | 6.67 | 6.65 | 6.55 | 0.00 | 0.00 | 0.00 |
| ubiquinol-cytochrome c reductase, complex III subunit XI | 11757334_a_at | UQCR11 | 7.06 | 7.27 | 7.26 | 7.25 | 0.00 | 0.00 | 0.00 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for non-invasive collection of gingival samples comprising:
   using a collection device oriented parallel to the gum line of a specific tooth; from a subject collecting said gingival samples
   detaching a portion of the collection device from the collection device and placing into a container;
   extracting protein and metabolite from the portion of the collecting device.

2. The method of claim 1 wherein the collection device is at least one of an interdental gum brush or buccal brush.

3. The method of claim 1 wherein the container contains extraction buffer.

4. The method of claim 3 wherein the extraction buffer is at least one of Dulbecco's phosphate-buffered saline or RNAlater.

5. A method for extraction from gingival brush samples comprising:
   using a collection device oriented parallel to the gum line of a specific tooth; from a subject collecting said gingival samples
   a portion of the collection device is detached from the collection device and placed into a container containing extraction buffer;
   removing the collection device from the container; and extracting a biomarker.

6. The method of claim 5, wherein the extracted biomarker is analyzed with analytical procedures that quantify the levels of at least one of metabolite.

7. The method of claim 6, wherein a metabolite is at least one of a metabolite produced by: lipid metabolism, protein and amino acid metabolism, carbohydrate metabolism, nuclear acid metabolism, or oxidative phosphorylation.

8. The method of claim 6, wherein the method of analysis is at least one of: immunoassay, gradient hydrophilic interaction liquid chromatography with tandem mass spectrometry (HILIC/MS/MS), enzymatic assay; or colorimetric assay.

9. The method of claim 6, wherein the metabolite is at least one of: citrulline, ornithine, arginine, succinate, malate and fumarate, deoxycarnitine or pyroglutamine.

10. The method of claim 6, wherein the metabolite is at least one of: 13-HODE (13-hydroxyoctadecadienoic acid), 9-HODE, asparagylleucine, arginylphenylalanine, valylvaline, valine, tyrosine, tryptophan, arginylleucine, trehalose, threonylphenylalanine, threonylleucine, alanine, spermidine, 2-methylbutyrylcarnitine (C5), serylisoleucine, pyroglutamine, adenosine 5'-monophosphate, propionylcarnitine, proline, 1-oleoylglycerophosphoethanolamine, phosphate, palatinitol, mannitol, maltotriose, maltose, lysylphenylalanine, lysylleucine, leucylleucine, leucine, glycerol, lauryl sulfate, glutathione, oxidized glutathione, glutamine, fructose, erythritol, or 1-arachidonoylglycerophosphoethanolamine.

\* \* \* \* \*